US012605447B2

(12) United States Patent
Marx et al.

(10) Patent No.: US 12,605,447 B2
(45) **Date of Patent: *Apr. 21, 2026**

(54) STABLE FORMULATIONS FOR RADIONUCLIDE COMPLEXES

(71) Applicant: ITM SOLUCIN GMBH, Garching bei München (DE)

(72) Inventors: Sebastian Marx, Dachau (DE); Oliver Leib, Ismaning (DE); Luke Heames, Unterschleißheim (DE); Elena Maria Andreolli, Pavia (IT)

(73) Assignee: ITM Solucin GmbH, Garching bei München (DE)

(*) Notice: Subject to any disclaimer, the term of this patent is extended or adjusted under 35 U.S.C. 154(b) by 0 days.

This patent is subject to a terminal disclaimer.

(21) Appl. No.: 19/028,880

(22) Filed: Jan. 17, 2025

(65) Prior Publication Data

US 2025/0170243 A1 May 29, 2025

Related U.S. Application Data

(63) Continuation of application No. 18/254,122, filed as application No. PCT/EP2021/082812 on Nov. 24, 2021.

(30) Foreign Application Priority Data

Nov. 25, 2020 (WO) ................ PCT/EP2020/083363

(51) Int. Cl.
*A61K 47/22* (2006.01)
*A61K 51/08* (2006.01)

(52) U.S. Cl.
CPC ............ *A61K 47/22* (2013.01); *A61K 51/088* (2013.01); *A61K 2121/00* (2013.01)

(58) Field of Classification Search
CPC ........ A61K 47/00; A61K 47/22; A61K 51/00; A61K 51/08; A61K 51/088; A61K 2121/00; A61K 9/0019; A61K 9/0021; A61K 9/08; A61K 47/12; A61K 51/082
See application file for complete search history.

(56) References Cited

U.S. PATENT DOCUMENTS

| | | | | |
|---|---|---|---|---|
| 10,596,278 | B2 * | 3/2020 | de Palo | A61K 47/22 |
| 10,756,278 | B2 | 8/2020 | Claridge et al. | |

FOREIGN PATENT DOCUMENTS

| | | | |
|---|---|---|---|
| EP | 2862857 | A1 | 4/2015 |
| WO | 2013022797 | A1 | 2/2013 |
| WO | 2014143736 | A1 | 9/2014 |
| WO | 2015055318 | A1 | 4/2015 |
| WO | 2018215627 | A1 | 11/2018 |
| WO | 2020109523 | A1 | 6/2020 |

OTHER PUBLICATIONS

International Search Report and Written Opinion for Application No. PCT/EP2021/082812, mailed Feb. 25, 2022, 8 pages.

Iori Michele et al: Labelling of 90Y- and 177Lu-DOTA-Bioconjugates for Targeted Radionuclide Therapy: A Comparison among Manual, Semiautomated, and Fully Automated Synthesis, Contrast Media & Molecular Imaging, vol. 2017 May 25, 2017 (May 25, 2017), pp. 1-12, XP055826873, GB ISSN: 1555-4309, DOI: 10.1155/2017/8160134 Retrieved from the Internet: URL:https://www.ncbi.nlm.nih.gov/pmc/artic les/PMC5612754/pdf/CMMI2017-8160134.pdf.

Singh, J. et al., "Stability Constants of Metal Complexes in Solution," InTech Open, 2019, DOI: http://dx.doi.org/10.5772/intechopen.90183, 19 pages.

Liu, S., et al., "Ascorbic Acid: Useful as a Buffer Agent and Radiolytic Stabilizer for Metalloradiopharmaceuticals," Bioconjugate Chem., 2003, pp. 1052-1056.

Examination Report for European Application No. EP21815203.1, as issued by the European Patent Office Feb. 25, 2025.

Office Action and Search Report issued by the Russian Patent Office for RU2023116057/04, mailed Apr. 3, 2025.

Office Action for corresponding Russian Patent Application No. 2023116057/04(034298), Oct. 7, 2025 (Russian language).

English language translation of Office Action for corresponding Russian Patent Application No. 2023116057/04 (034298), Oct. 7, 2025.

Bakhareva, A.A. et al., Development of New Chelating Agents for Radiopharmaceuticals, Advances in Chemistry and Chemical Technology, 2019, No. 7 (217), p. 18, 2 pages (In Russian, cited in the Office Action for corresponding Russian Patent Application No. 2023116057/04(034298), Oct. 7, 2025).

Maus, S. et al., Aspects on radiolabeling of 177Lu-DOTA-TATE: After C18 purification re-addition of ascorbic acid is required to maintain radiochemical purity, International Journal of Diagnostic Imaging, Feb. 21, 2014, vol. 1, No. 1, pp. 5-12.

De Blois, E. et al., Effectiveness of Quenchers to Reduce Radiolysis of (111)In- Or (177)Lu-labelled Methionine-Containing Regulatory Peptides. Maintaining Radiochemical Purity as Measured by HPLC., Curr Top Med Chem. 2012;12(23):2677-85.

(Continued)

*Primary Examiner* — D. L. Jones

(74) *Attorney, Agent, or Firm* — Julie K. Staple; Fishman Stewart PLLC

(57) ABSTRACT

The present invention provides a pharmaceutical composition comprising a radiolabeled complex comprising a radionuclide and a targeting molecule linked to a chelating agent; and a stabilizer against radiolytic degradation comprising ascorbic acid and/or a salt thereof; wherein the composition does not comprise gentisic acid or a salt thereof. The pharmaceutical composition of the present invention provides high stability against radiolytic degradation. The present invention also provides a process for preparing such a pharmaceutical composition.

20 Claims, 6 Drawing Sheets

Specification includes a Sequence Listing.

(56) References Cited

OTHER PUBLICATIONS

Breeman, W. A.P., Practical Aspects of labeling DTPA- and DOTA-Peptides with 90Y, 111In, 177Lu, and 68Ga for Peptide-Receptor Scintigraphy and Peptide-Receptor Radionuclide Therapy in Preclinical and Clinical Applications, The University of New Mexico Health Sciences Center, vol. 16, Lesson 5: Nov. 16, 2012, 34 pages.
Kerdjoudj, R. et al., Scandium(III) complexes of monophosphorus acid DOTA analogues: a thermodynamic and radiolabelling study with 44Sc from cyclotron and from a 44Ti/44Sc generator, Dalton Trans., 2016, 45, 1398-1409.
Chang, S., Overview of Prostate-Specific Membrane Antigen, Rev Urol., 2004, 6 (Suppl 10): S13-S18.
Bouchelouche, K. et al., Prostate Specific Membrane Antigen-A Target for Imaging and Therapy with Radionuclides, Discov Med., Jan. 2010; 9(44): 55-61.
Hillier, S., et al., Preclinical Evaluation of Novel Glutamate-Urea-Lysine Analogues That Target Prostate-Specific Membrane Antigen as Molecular Imaging Pharmaceuticals for Prostate Cancer, Cancer Res., Sep. 1, 2009;69 (17):6932-40.
Beneová et al., Preclinical Evaluation of a Tailor-Made DOTA-Conjugated PSMA Inhibitor with Optimized Linker Moiety for Imaging and Endoradiotherapy of Prostate Cancer, J. Nucl. Med, Apr. 16, 2015, 56:914-920.
Barrett, J.A. et al., First-in-Man Evaluation of 2 High-Affinity PSMA-Avid Small Molecules for Imaging Prostate Cancer, J Nucl Med., Jan. 9, 2013, 54:380-387.
Zechmann, C. et al., Radiation dosimetry and first therapy results with a 1241/131 I-labeled small molecule (MIP-1095) targeting PSMA for prostate cancer therapy, Eur J Nucl Med Mol Imaging, Feb. 28, 2014, 41:1280-1292.
Afshar-Oromieh, A. et al., The Theranostic PSMA Ligand PSMA-617 in the Diagnosis of Prostate Cancer by PET/ CT: Biodistribution in Humans, Radiation Dosimetry, and First Evaluation of Tumor Lesions, J Nucl Med., Aug. 20, 2015, 56:1697-1705.
Weineisen, M. et al., 68Ga- and 177Lu-Labeled PSMA I&T: Optimization of a PSMA-Targeted Theranostic Concept and First Proof-of-Concept Human Studies, J Nucl Med., Jun. 18, 2015. 56:1169-1176.
Robu, S. et al., Preclinical Evaluation and First Patient Application of 99mTc-PSMA-I&S for SPECT Imaging and Radioguided Surgery in Prostate Cancer, J Nucl Med., 2017; 58:235-242.
Chen, Y. et al., 2-(3-{1-Carboxy-5-[(6-[18F]Fluoro-Pyridine-3-Carbonyl)-Amino]-Pentyl}-Ureido)-Pentanedioic Acid, [18F]DCFPyL, a PSMA-Based PET Imaging Agent for Prostate Cancer, Clin Cancer Res., Dec. 15, 2011, 17 (24):7645-7653.
Giesel, F.L. et al., Eur J Nucl Med Molecular Imaging, F-18 labelled PSMA-1007: biodistribution, radiation dosimetry and histopathological validation of tumor lesions in prostate cancer patients, 2017; 44:678-688.
Kelly, J. M. et al., Dual-Target Binding Ligands with Modulated Pharmacokinetics for Endoradiotherapy of Prostate Cancer., J Nucl Med., Sep. 2017, 58(9):1442-1449. doi: 10.2967/jnumed.116.188722.
Choy, C. J. et al., 177Lu-Labeled Phosphoramidate-Based PSMA Inhibitors: The Effect of an Albumin Binder on Biodistribution and Therapeutic Efficacy in Prostate Tumor-Bearing Mice, Theranostics, Apr. 27, 2017; 7(7): 1928-1939.
Capello, A. et al., Tyr3-octreotide and Tyr3-octreotate radiolabeled with 177Lu or 90Y: peptide receptor radionuclide therapy results in vitro, Cancer Biotherapy Radiopharm, Oct. 2003; 18(5): 761-8.
Guo, W. et al., 99mTc-HyNIC-Folate: A Novel Receptor-Based Targeted Radiopharmaceutical for Tumor Imaging, J Nucl Med. 1999; 40:1563-1569.
Mathias, C. J. et al., Synthesis of [99mTc]DTPA-Folate and Its Evaluation as a Folate-Receptor-Targeted Radiopharmaceutical, Bioconjug Chem., 2000, 11:253-257.
Leamon, C. P. et al., Synthesis and Biological Evaluation of EC20: A New Folate-Derived, 99mTc-Based Radiopharmaceutical, Bioconjugate Chem., 2002, 13:1200-1210.
Reddy, J. A. et al., Preclinical Evaluation of 99mTc-EC20 for Imaging Folate Receptor-Positive Tumors, J Nucl. Med., May 2004, 45(5):857-866.
Müller, C. et al., Preclinical evaluation of novel organometallic 99mTc-folate and 99mTc-pteroate radiotracers for folate receptor-positive tumour targeting, Eur J Nucl Med Mol Imaging, Sep. 2006; 33(9):1007-1016.
Müller, C. et al., Synthesis and in Vitro/in Vivo Evaluation of Novel 99mTc(CO)3-Folates, Bioconjug Chem., Apr. 28, 2006; 17:797-806.
Siegel, B. A. et al., Evaluation of 111In-DTPA-Folate as a Receptor-Targeted Diagnostic Agent for Ovarian Cancer: Initial Clinical Results, J Nucl Med., May 2003, 44(5):700-707.
Mathias, C. J. et al., Receptor-Mediated Targeting of 67Ga-Deferoxamine-Folate to Folate-Receptor-Positive Human KB Tumor Xenografts, Nucl Med Biol. 1999; 26:23-25.
Mathias, C. J. et al., Preparation of 66Ga- and 68Ga-labeled Ga(III)-deferoxamine-folate as potential folate-receptor-targeted PET radiopharmaceuticals, Nucl Med Biol., 2003, 30:725-731.
Bettio, A. et al., Synthesis and Preclinical Evaluation of a Folic Acid Derivative Labeled with 18F for PET Imaging of Folate Receptor-Positive Tumors, J Nucl Med., Jul. 2006; 47(7):1153-1160.
Baum, R. P. et al., 177Lu-3BP-227 for Neurotensin Receptor 1-Targeted Therapy of Metastatic Pancreatic Adenocarcinoma: First Clinical Results, The Journal of Nuclear Medicine, 59(5):809-814, May 2018.
Zhang, H. et al., Synthesis and Evaluation of Bombesin Derivatives on the Basis of Pan-Bombesin Peptides Labeled with Indium-111, Lutetium-177, and Yttrium-90 for Targeting Bombesin Receptor-Expressing Tumors, Cancer Res, Sep. 15, 2004; 64:6707-6715.
Bodei, L et al., 177Lu-AMBA Bombesin analogue in hormone refractory prostate cancer patients: a phase I escalation study with single-cycle administrations, Eur J Nucl Med Mol Imaging, 2007, 34(suppl 2): S221, Abstract 463.
Hennig, I. M. et al., Substance-P Receptors in Human Primary Neoplasms: Tumoral and Vascular Localization, Int J Cancer, 1995, 61:786-792.
Kneifel, S. et al., Individual voxelwise dosimetry of targeted 90Y-labelled substance P radiotherapy for malignant gliomas, Eur J Nucl Med Mol Imaging, Jan. 31, 2007, 34:1388-1395.
Cordier, D. et al., Targeted alpha-radionuclide therapy of functionally critically located gliomas with 213Bi-DOTA- [Thi8, Met(O2)11]-substance P: a pilot trial, Eur J Nucl Med Mol Imaging, Feb. 16, 2010, 37:1335-1344.
Basu, S. et al. Peptide Receptor Radionuclide Therapy of Neuroendocrine Tumors, Semin Nucl Med, 50:447-464, 2020.

* cited by examiner

Integration Results

| No. | Peak Name | Retention Time min | Rel. Ret.Time | Area mV*min | Relative Area % | Height mV |
|---|---|---|---|---|---|---|
| 1 | 177LuCl3 | 1,230 | 0,13 | 0,022 | 0,08 | 0,141 |
| 2 | | 8,888 | 0,92 | 0,025 | 0,10 | 0,197 |
| 3 | | 9,350 | 0,97 | 0,067 | 0,25 | 0,522 |
| 4 | 177Lu-DOTATOC | 9,627 | 1,00 | 26,475 | 99,02 | 190,230 |
| 5 | | 10,633 | 1,11 | 0,147 | 0,55 | 0,737 |
| **Total:** | | | | **26,737** | **100,00** | **191,83** |

Integration Results

| No. | Peak Name | Retention Time min | Rel. Ret.Time | Area mV*min | Relative Area % | Height mV |
|---|---|---|---|---|---|---|
| 1 | 177LuCl3 | 1,223 | 0,13 | 0,026 | 0,09 | 0,143 |
| 2 | | 7,773 | 0,80 | 0,026 | 0,09 | 0,181 |
| 3 | | 8,038 | 0,83 | 0,035 | 0,12 | 0,267 |
| 4 | | 8,917 | 0,92 | 0,090 | 0,30 | 0,354 |
| 5 | | 9,070 | 0,94 | 0,052 | 0,17 | 0,321 |
| 6 | | 9,442 | 0,97 | 0,034 | 0,11 | 0,246 |
| 7 | 177Lu-DOTATOC | 9,688 | 1,00 | 29,291 | 98,01 | 210,221 |
| 8 | | 10,738 | 1,11 | 0,140 | 0,47 | 0,735 |
| 9 | | 11,187 | 1,15 | 0,041 | 0,14 | 0,337 |
| 10 | | 16,673 | 1,72 | 0,151 | 0,51 | 1,006 |
| Total: | | | | 29,885 | 100,00 | 213,81 |

Integration Results

| No. | Peak Name | Retention Time min | Rel. Ret.Time | Area mV*min | Relative Area % | Height mV |
|---|---|---|---|---|---|---|
| 1 | 177LuCl3 | 1,240 | 0,13 | 0,052 | 0,15 | 0,229 |
| 2 | | 8,878 | 0,92 | 0,050 | 0,14 | 0,586 |
| 3 | | 8,928 | 0,92 | 0,044 | 0,12 | 0,401 |
| 4 | | 9,457 | 0,98 | 0,057 | 0,16 | 0,482 |
| 5 | 177Lu-DOTATOC | 9,697 | 1,00 | 35,372 | 98,83 | 254,756 |
| 6 | | 10,745 | 1,11 | 0,215 | 0,60 | 0,823 |
| **Total:** | | | | **35,790** | **100,00** | **257,28** |

Chromatogram

Integration Results

| No. | Peak Name | Retention Time min | Rel. Ret.Time | Area mV*min | Relative Area % | Height mV |
|---|---|---|---|---|---|---|
| 1 | 177LuCl3 | 1,225 | 0,13 | 0,124 | 0,45 | 0,789 |
| 2 | | 6,320 | 0,55 | 0,068 | 0,25 | 0,498 |
| 3 | | 7,138 | 0,74 | 0,054 | 0,20 | 0,348 |
| 4 | | 7,315 | 0,75 | 0,063 | 0,23 | 0,472 |
| 5 | | 8,007 | 0,82 | 0,081 | 0,29 | 0,574 |
| 6 | | 8,407 | 0,87 | 0,233 | 0,85 | 1,605 |
| 7 | | 8,840 | 0,91 | 0,469 | 1,71 | 3,236 |
| 8 | | 9,103 | 0,94 | 0,064 | 0,23 | 0,466 |
| 9 | | 9,442 | 0,97 | 0,250 | 0,91 | 1,694 |
| 10 | 177Lu-DOTATOC | 9,707 | 1,00 | 25,895 | 94,23 | 184,752 |
| 11 | | 10,723 | 1,10 | 0,181 | 0,66 | 0,918 |

STABLE FORMULATIONS FOR RADIONUCLIDE COMPLEXES

REFERENCE TO RELATED APPLICATIONS

This application is a continuation of U.S. patent application Ser. No. 18/254,122, filed May 23, 2023, which is a U.S. national stage application of PCT/EP2021/082812, filed Nov. 24, 2021, which claims priority to PCT Patent Application No. PCT/EP2020/083363, filed Nov. 25, 2020; the entire content of each of these applications is incorporated herein by reference.

SEQUENCE LISTING

The instant application contains a Sequence Listing which has been submitted electronically in XML format and is hereby incorporated by reference in its entirety. Said XML format Sequence Listing, created on Sep. 3, 2025, is named ITMS0001NA.xml and is 92440 bytes in size.

FIELD OF THE INVENTION

The present invention relates to the field of radiopharmaceutical formulations, in particular to formulations ensuring the stability of radionuclide complexes and to methods of preparing such formulations.

BACKGROUND OF THE INVENTION

Radiopharmaceuticals are drugs, which contain radioactive isotopes (radionuclides). Radiopharmaceuticals can be used to treat various conditions, including cancers, blood disorders and hyperthyroidism. In radionuclide therapy of cancer, a molecule labeled with a radionuclide is used to deliver a toxic level of radiation to disease sites. Accordingly, the molecule is used to "target" the disease site, e.g. specific cancer cells. Accordingly, the radionuclide complex combines the specificity of cancer cell targeting with the known antitumor effects of ionizing radiation. Thereby, not only the primary tumor site, but also its metastases can be targeted. The choice of the molecule that carries the radiation to the tumor is usually determined by its selectivity and affinity to the tumor's target structures, such as antigens or receptors. Even if a target structure is not selective for a certain kind of cancer, overexpressed target structures are of interest, because they allows the delivery of the radionuclide complex after its systemic administration in high concentration to those (overexpressing) target cells while leaving other cells (with no or minor expression only) essentially unaffected. Radionuclides are usually linked to the targeting molecule through chelating agents. Thereby, strong complexes with the metal ion of the radionuclide can be formed. The radioactive decay of the radionuclides can cause significant damage to cancer cells by releasing high energy electrons, positrons or alpha particles as well as gamma rays at the target site.

However, radioactive decay of the radionuclide occurs constantly, including during manufacturing and storage of the radionuclide complex. The high energy emitted in radioactive decay can induce the cleavage of the chemical bonds of the radionuclide complex, thereby leading to partial destruction of the drug due to its radioactivity. The radiolytic degradation of the targeting molecule of the radionuclide complex may result in a reduced specificity of the radionuclide complex, thereby leading to a decrease in its efficacy and/or to an increase in undesired side effects.

The stability of radiopharmaceuticals is therefore usually restricted to a few hours or days only. This results in various challenges regarding the manufacture, storage and transport of radiopharmaceuticals. Therefore, for the application of radiopharmaceuticals only a small window is available after manufacturing.

In order to reduce this problem, usually antioxidants, such as gentisic acid, ethanol, ascorbic acid and methionine, are added to the formulation of the radionuclide complex. However, in particular for peptides labelled with $^{177}$Lu, such as DOTATOC (edotreotide) and DOTATATE (oxodotreotide), often complex mixtures of antioxidants or specific time points of their addition are required to obtain the desired effect over an acceptable period of time. For example, Maus et al. reports the addition of ascorbic acid after radiolabeling and purification of [177Lu]Lu-DOTATATE (Stephan Maus et al. Aspects on radiolabeling of 177Lu-DOTA-TATE: After C18 purification re-addition of ascorbic acid is required to maintain radiochemical purity, International Journal of Diagnostic Imaging, 2014, Vol. 1, No. 1). U.S. Pat. No. 10,756,278 B2 requires a complex mixture of gentisic acid, ascorbic acid, and EDTA after radiolabeling to obtain the desired stability against radiolysis of 95% at 72 hours after synthesis. De Blois et al. and Breeman et al. even suggest the addition of a mixture of 50 mM ascorbic acid, 10% (v/v) ethanol and 50 mM L-methionine (Erik de Blois et al. Effectiveness of Quenchers to Reduce Radiolysis of (111)In-Or (177)Lu-labelled Methionine-Containing Regulatory Peptides. Maintaining Radiochemical Purity as Measured by HPLC. Curr Top Med Chem. 2012; 12(23):2677-85; Wouter A. P. Breeman; Practical Aspects of labeling DTPA- and DOTA-Peptides with 90Y, 111In, 177Lu, and 68Ga for Peptide-Receptor Scintigraphy and Peptide-Receptor Radionuclide Therapy in Preclinical and Clinical Applications The University of New Mexico Health Sciences Center, VOLUME 16, LESSON 5: Nov. 16, 2012). According to these reports, for $^{177}$Lu-labelled peptides, the stabilizer, or the second or third stabilizing component, is added only after radiolabeling in acetate or HEPES buffer.

In view of the above, it is the object of the present invention to overcome the drawbacks outlined above and to provide a novel formulation for a radionuclide complex, which ensures increased stability of the radionuclide complex over an increased period of time. In particular, such a formulation contains as few components as possible and is well-tolerated upon parenteral injection. Moreover, the antioxidant used in the formulation may also serve as pH-modulator/buffer (in particular in a pH-range acceptable for parenteral injections, such as pH 4.5-8), such that complicated mixtures can be avoided. Additionally, the antioxidant used in the formulation may also serve as buffer for radiolabeling resulting in high radiolabeling yields, which further avoids complicated mixtures.

This object is achieved by means of the subject-matter set out below and in the appended claims.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±20%, preferably x±10%, more preferably x±5%, even more preferably x±2% and still more preferably x±1%.

Pharmaceutical Composition

In a first aspect the present invention provides a pharmaceutical composition comprising:

(a) a radiolabeled complex comprising (i) a radionuclide and (ii) a targeting molecule linked to a chelating agent; and (b) a stabilizer against radiolytic degradation comprising ascorbic acid and/or a salt thereof;

wherein the composition does not comprise gentisic acid or a salt thereof.

The present inventors have surprisingly found that such a formulation of the radionuclide complex ensures increased stability of the radionuclide complex over an increased period of time, in particular at least 96 hours. Interestingly, the increased stability/shelf life can be achieved with a formulation containing fewer components, and thus less complex, as compared to prior art formulations for radionuclide complexes. In particular, the antioxidant used in the formulation may also serve as pH-modulator/buffer (in particular in a pH-range acceptable for parenteral injections, such as pH 4.5-8), such that complicated mixtures can be avoided. Additionally, the antioxidant used in the formulation may also serve as buffer for radiolabeling resulting in high radiolabeling yields, which further avoids complicated mixtures. Nevertheless, the composition is well-tolerated, e.g. upon parenteral injection.

Radiolabeled Complex

The radiolabeled complex comprising (i) the radionuclide and (ii) the targeting molecule linked to a chelating agent is typically formed by (i) the radionuclide and (ii) the targeting molecule linked to a chelating agent, for example in step (i) of a process as described herein below. Various radiolabeled complexes are known in the art. Particularly preferred examples of radiolabeled complexes are described in WO 2018/215627 A1, which is incorporated herein by reference. Further examples for commercially available radiolabeled complexes include [$^{177}$Lu]Lu-DOTATATE (Lutathera®), [$^{131}$I]I-mIBG, $^{153}$Sm-EDTMP (Quadramet®), $^{89}$Sr chloride, $^{90}$Y-loaded microspheres (TheraSphere™ or SIR-Sphere®), and yttrium-90 ibritumomab tiuxetan (Zevalin®).

Radionuclide

Various radionuclides (radioisotopes) are known to be useful in the field of radionuclide therapy. In particular, the term "radionuclide" (or "radioisotope") refers to isotopes of natural or artificial origin with an unstable neutron to proton ratio that disintegrates with the emission of corpuscular (i.e. protons (alpha-radiation) or electrons (beta-radiation) or electromagnetic radiation (gamma-radiation). In other words, radionuclides undergo radioactive decay. Said radionuclide which may preferably be useful for cancer imaging or therapy. Non-limiting examples of suitable radionuclides include $^{94}$Tc, $^{99m}$Tc, $^{90}$In, $^{111}$In, $^{67}$Ga, $^{68}$Ga, $^{86}$Y, $^{90}$Y, $^{177}$Lu, $^{151}$Tb, $^{186}$Re, $^{188}$Re, $^{64}$Cu, $^{67}$Cu, $^{55}$Co, $^{57}$Co, $^{43}$Sc, $^{44}$Sc, $^{47}$Sc, $^{225}$Ac, $^{213}$Bi, $^{212}$Bi, $^{212}$Pb, $^{227}$Th, $^{153}$Sm, $^{166}$Ho, $^{152}$Gd, $^{153}$Gd, $^{157}$Gd, and $^{166}$Dy. Accordingly, the radionuclide may be any one of the before-mentioned examples. The choice of suitable radionuclides may depend inter alia on the chemical structure and chelating capability of the chelating agent, and the intended application of the resulting (complexed) conjugate (e.g. diagnostic vs. therapeutic). For instance, the beta-emitters such as $^{90}$Y, $^{131}$I, $^{161}$Tb and $^{177}$Lu may be used for systemic radionuclide therapy. For example, DOTA, as chelating agent, may advantageously enable the use of $^{68}$Ga, $^{43,44,47}$Sc, $^{177}$Lu, $^{161}$Tb, $^{225}$Ac, $^{213}$Bi, $^{212}$Bi, or $^{212}$Pb as radionuclides.

Preferably, the radionuclide may be $^{44}$Sc. It is also preferred that the radionuclide may be $^{64}$Cu. In some preferred embodiments, the radionuclide may be $^{68}$Ga.

Even more preferably, the radionuclide is $^{177}$Lu (Lutetium-177).

In some embodiments, the radionuclide, in particular $^{177}$Lu, is present in the pharmaceutical composition at a concentration providing volumetric radioactivity of from 0.25 to 0.6 GBq/ml, preferably 0.3 to 0.55 GBq/ml, more preferably 0.35 to 0.5 GBq/ml, even more preferably 0.4 to 0.45 GBq/ml, such as about 0.42 GBq/ml.

Chelating Agent

In the radiolabeled complex, the radionuclide metal ion is usually forming a non-covalent bond with functional groups of the chelating agent, e.g. amines or carboxylic acids. Typically, the chelating agent has at least two such complexing functional groups to be able to form a chelate complex.

As used herein, the term “chelating agent” (also referred to as “chelator”) refers to polydentate (multiple bonded) ligands capable of forming two or more separate coordinate bonds with (“coordinating”) a central (metal) ion, in particular the radionuclide metal ion. Specifically, such molecules or molecules sharing one electron pair may also be referred to as “Lewis bases”. The central (metal) ion is usually coordinated by two or more electron pairs to the chelating agent. The terms, “bidentate chelating agent”, “tridentate chelating agent”, and “tetradentate chelating agent” are known in the art and refer to chelating agents having two, three, and four electron pairs, respectively, which are readily available for simultaneous donation to a metal ion coordinated by the chelating agent. Usually, the electron pairs of a chelating agent forms coordinate bonds with a single central (metal) ion; however, in certain examples, a chelating agent may form coordinate bonds with more than one metal ion, with a variety of binding modes being possible.

The terms “coordinating” and “coordination” refer to an interaction in which one multi-electron pair donor coordinatively bonds (is “coordinated”) to, i.e. shares two or more unshared pairs of electrons with, one central (metal) ion.

The chelator or chelating agent is preferably a macrocyclic bifunctional chelator having a metal chelating group at one end and a reactive functional group at the other end, which is capable to bind to other moieties, e.g. peptides. Preferably, the chelator may be selected such that the chelator forms a square bi-pyramidal complex for complexing the radionuclide. In another embodiment, the chelator does not from a planar or a square planar complex.

The chelating agent may be selected based on its ability to coordinate the desired central (metal) ion, usually the radionuclide as described herein. Preferably, the chelating agent is selected from 1,4,7,10-tetraazacyclododecane-1,4,7,10-tetraacetic acid (DOTA), N,N"-bis[2-hydroxy-5-(carboxyethyl)-benzyl]ethylenediamine-N,N"-diacetic acid (HBED-CC), 1,4,7-triazacyclononane-1,4,7-triacetic acid (NOTA), 2-(4,7-bis(carboxymethyl)-1,4,7-triazonan-1-yl) pentanedioic acid (NODAGA), 2-(4,7,10-tris(carboxymethyl)-1,4,7,10-tetraazacyclododecan-1-yl)-pentanedioic acid (DOTAGA), 1,4,7-triazacyclononane phosphinic acid (TRAP), 1,4,7-triazacydononane-1-[methyl(2-carboxyethyl)-phosphinic acid]-4,7-bis[methyl(2-hydroxymethyl) phosphinic acid] (NOPO), 3,6,9,15-tetraazabicyclo[9,3,1] pentadeca-1(15),11,13-triene-3,6,9-triacetic acid (PCTA), N'-{5-[Acetyl(hydroxy)amino]pentyl}-N-[5-({4-[(5-aminopentyl)(hydroxy)amino]-4-oxobutanoyl}amino)pentyl]-N-hydroxysuccinamide (DFO), ethylenediaminetetraacetic acid (EDTA), nitrilotriacetic acid (NTA), 1,4,7,10-Tetraazacyclododecane-1,4,7-triacetic acid (DO3A), and Diethylenetriaminepentaacetic acid (DTPA).

Accordingly, the chelating agent may be characterized by one of the following formulas (1a)-(1kk):

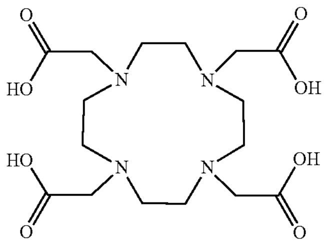

DOTA (1a)

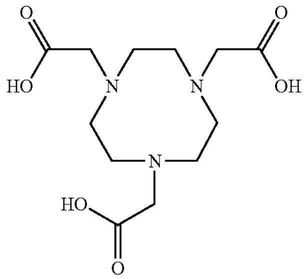

NOTA (1b)

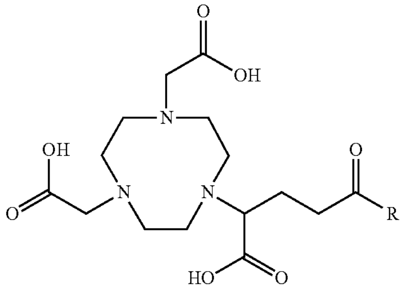

NODAGA (1c)

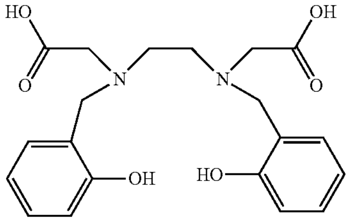

HBED (1d)

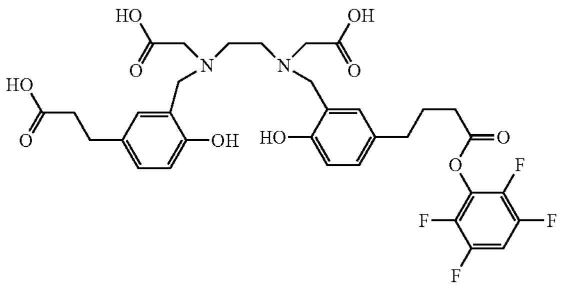

HBED-CC TFP (1e)

-continued
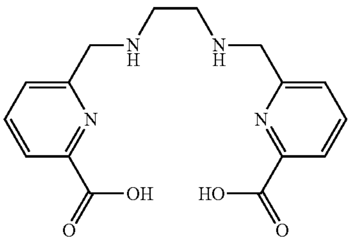
$H_2$DEPDPA (1f)
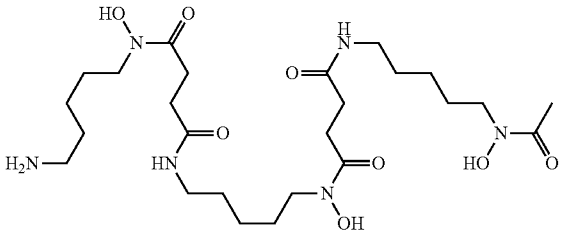
DFO-B (1g)
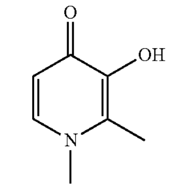
Deferiprone (1h)
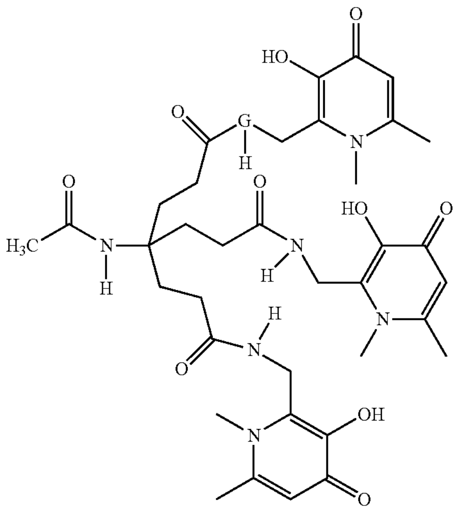
CP256 (1i)
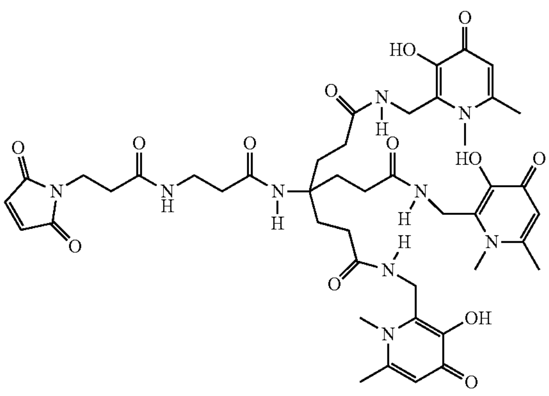
YM103 (1j)
-continued
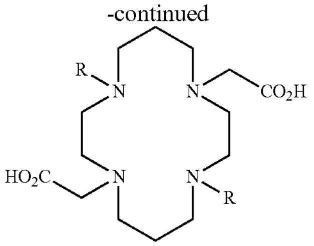
R = H TETA (1k)
R = $CH_2CO_2H$ TE2A (1l)
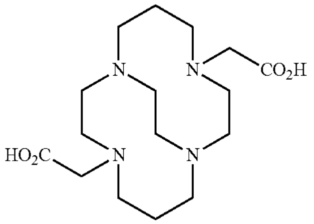
CB-TE2A (1m)
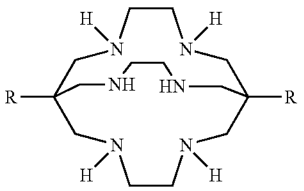
R = H Sar (1n)
R = $NH_2$ DiAmSar (1o)
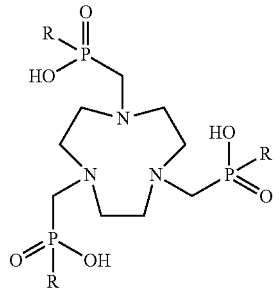
R = H TRAPH (1p)
R = $(CH2)_2CO_2H$ TRAP-Pr (1q)
R = $CH_2OH$ TRAP-OH (1r)
R = phenyl TRAP-Ph (1s)
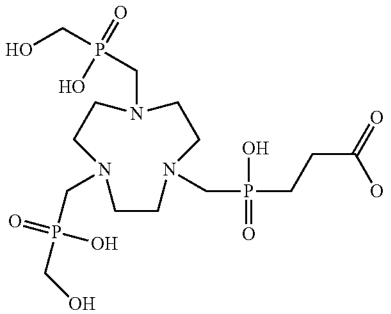
NOPO (1t)

-continued
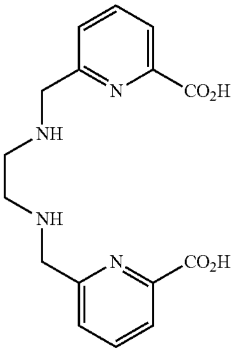
DEDPA (BCPE) (1u)
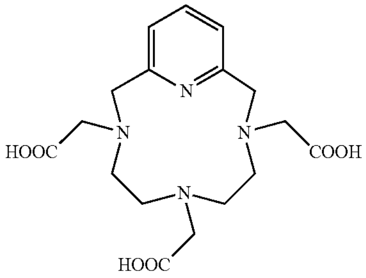
PCTA (1v)
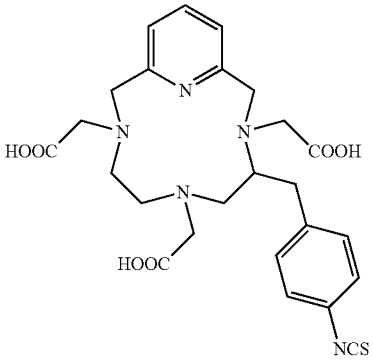
177 (1w)
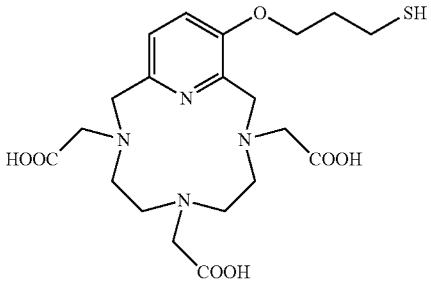
178 (1x)
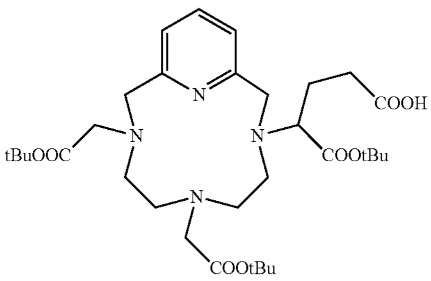
179 (1y)
-continued
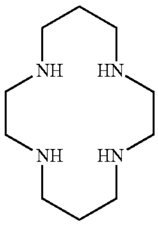
Cyclam (1z)
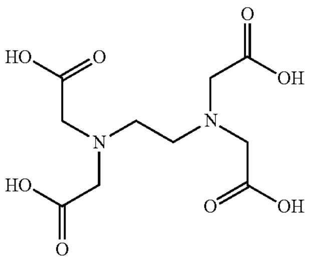
EDTA (1aa)
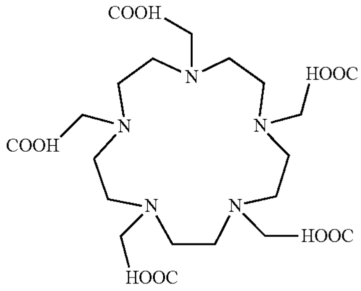
PEPA (1bb)
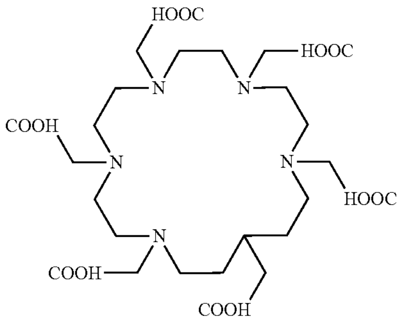
HEHA (1cc)
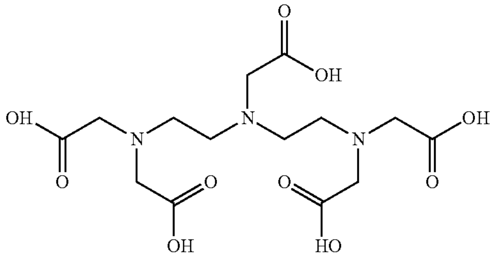
DTPA (1dd)

-continued

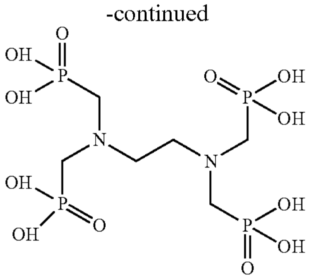

EDTMP (1ee)

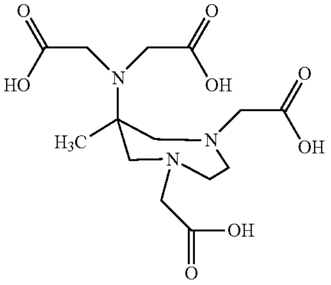

AAZTA (1ff)

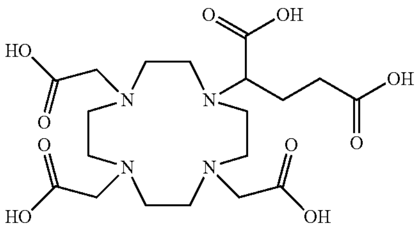

DOTAGA
DOTAGA (1gg)

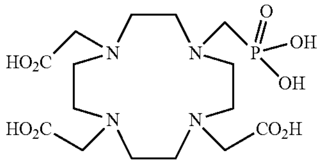

DO3AP (1hh)

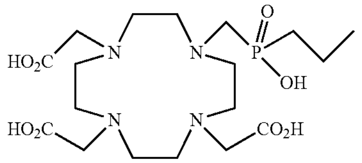

DO3AP$^{PrA}$ (1ii)

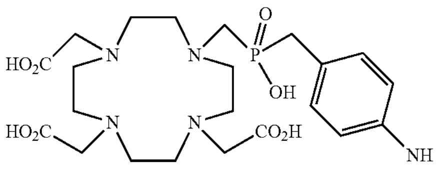

DO3AP$^{ABn}$ (1jj)

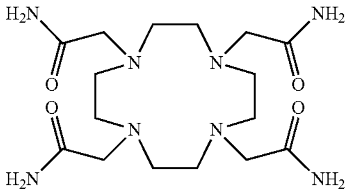

DOTAM (1kk)

More preferably, the chelating agent may be DOTA (1,4,7,10-tetraazacyclododecane-1,4,7,10-tetraacetic acid, which may be characterized by Formula (1a)), NODAGA (2-(4,7-bis(carboxymethyl)-1,4,7-triazonan-1-yl)-pentanedioic acid, which may be characterized by Formula (1c)), or derivatives thereof.

Other preferred chelators in the context of the present invention include N,N"-bis[2-hydroxy-5-(carboxyethyl) benzyl]ethylenediamine-N,N"-diacetic acid (HBED-CC), 1,4,7-triazacyclo-nonane-1,4,7-triacetic acid (NOTA), 2-(4,7,10-tris(carboxymethyl)-1,4,7,10-tetra-azacyclododecan-1-yl)-pentanedioic acid (DOTAGA), 1,4,7-triazacyclo-nonane phosphinic acid (TRAP), 1,4,7-triazacydo-nonane-1-[methyl(2-carboxyethyl)-phosphinic acid]-4,7-bis-[methyl(2-hydroxymethyl)-phosphinic acid] (NOPO), 3,6,9,15-tetra-azabicyclo[9,3,1]-pentadeca-1(15),11,13-triene-3,6,9-triacetic acid (PCTA), N'-{5-[Acetyl(hydroxy)amino]-pentyl}-N-[5-({4-[(5-aminopentyl)(hydroxy)amino]-4-oxobutanoyl}-amino)pentyl]-N-hydroxysuccinamide (DFO), and Diethylene-triaminepentaacetic acid (DTPA).

Particularly preferably, the chelating agent is DOTA. Advantageously, DOTA effectively forms complexes with diagnostic (e.g. $^{68}$Ga) and therapeutic (e.g. $^{90}$Y or $^{177}$Lu) radionuclides and thus enables the use of the same conjugate (targeting molecule linked to the chelating agent) for both imaging and therapeutic purposes, i.e. as a theragnostic agent. DOTA derivatives capable of complexing Scandium radionuclides ($^{43}$Sc, $^{44}$Sc, $^{47}$Sc), including DO3AP (which may be characterized by Formula (1hh)), DO3AP$^{PrA}$ (which may be characterized by Formula (4ii)), or DO3AP$^{ABn}$ (which may be characterized by Formula (4jj)) may also be preferred and are described in Kerdjoudj et al. Dalton Trans., 2016, 45, 1398-1409.

The chelating agent, for example DOTA, may be complexed with any known radionuclide (in particular with the radionuclide as described above) as a central (metal) ion. It is within the skill and knowledge of the skilled person in the art to select suitable combinations conjugates and radionuclides. In some embodiments, the chelator may be DOTA and the radionuclide may be $^{68}$Ga. In other embodiments, the chelator may be DOTA and the radionuclide may be $^{44}$Sc. In yet further embodiments, the chelator may be DOTA and the radionuclide may be $^{64}$Cu. In other embodiments, the chelator may be NODAGA and the radionuclide may be $^{64}$Cu. Particularly preferably, the chelator is DOTA and the radionuclide is $^{177}$Lu.

Targeting Molecule

As used herein, the term "targeting molecule" (also referred to as "targeting moiety" refers to a molecule, which is able to bind (specifically) to a "target", such as a target cell (e.g., a cancer cell). In particular, the "target" may be a molecule located at the cell surface of a target cell (e.g., a cancer cell). Such a surface molecule, to which the targeting molecule binds, may be, for example, a receptor located at the surface of the cell. In particular, the surface molecule is specific for or overexpressed by the target cell (e.g., a cell "marker"). The targeting molecule may bind, for example, to a disease (e.g., cancer) marker (which is expressed/located at the surface of the cell involved in the disease, e.g. a cancer cell). Thereby, the targeting molecule can guide the radionuclide specifically to the cell involved in the disease, e.g. a cancer cell. Accordingly, the targeting molecule is usually selected depending on the disease to be treated or diagnosed. In the context of a disease, e.g. cancer, the cells to be targeted with the radiolabeled complex, e.g. cancer cells, usually express specific molecules (or overexpress specific molecules), which may serve as "target" (surface molecule). The targeting molecule is typically selected such that it binds to said "targets" (surface molecules and, thus, target cells, e.g. cancer cells). The binding of the targeting molecule to the surface molecule may be reversible or irreversible. In some embodiments, the targeting molecule is a peptide or polypeptide or a modified peptide or polypeptide.

Various surface molecules, to which the targeting molecule may suitably bind, are known in the art. In the following, examples of receptors and cell surface molecules present on tumor cells, which may be a target structure for the targeting molecule, are described in detail. However, the target structures are not limited to the receptors and cell surface molecules described below. Further receptors and cell surface molecules present on cancer or other disease cells are contemplated as target structures for the targeting molecules. Moreover, further targeting molecules targeting the receptors and cell surface molecules present on cancer or other disease cells are contemplated.

Particularly suitable surface molecules are PSMA and a somatostatin receptor. Accordingly, the targeting molecule is preferably able to bind to PSMA or a somatostatin receptor.

PSMA-Targeting Compounds

Human Prostate-specific membrane antigen (PSMA) (also referred to as glutamate carboxypeptidase II (GCPII), folate hydrolase 1, folypoly-gamma-glutamate carboxypeptidase (FGCP), and N-acetylated-alpha-linked acidic dipeptidase I (NAALADase I)) is a type II transmembrane zinc metallopeptidase that is most highly expressed in the nervous system, prostate, kidney, and small intestine. It is considered a tumor marker in prostate cancer. The term "Human Prostate-specific membrane antigen" or "PSMA" as used herein preferably refers to the protein encoded by the human FOLH1 gene. More preferably, the term refers to the protein as characterized under UniProt Acc. No. Q04609 (entry version 186, last modified May 10, 2017), or functional variants, isoforms, fragments or (post-translationally or otherwise modified) derivatives thereof.

The PSMA-binding targeting molecule may generally be a binding entity capable of selectively (and optionally irreversibly) binding to (human) Prostate-Specific Membrane Antigen (e.g., as described in Chang Rev Urol. 2004; 6(Suppl 10): S13-S18). The PSMA targeting molecule is preferably chosen by its ability to confer selective affinity towards PSMA. Preferred PSMA binding moieties are described in WO 2013/022797 A1, WO 2015/055318 A1 and EP 2862857 A1, which are incorporated by reference in their entirety herein.

Accordingly, the PSMA targeting molecule may preferably be characterized by General Formula (2):

(2)

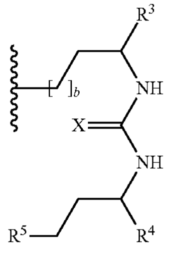

wherein

X is selected from O, N, S or P, $R^3$, $R^4$ and $R^5$ are each independently selected from —COH, —$CO_2H$, —$SO_2H$, —$SO_3H$, —$SO_4H$, —$PO_2H$, —$PO_3H$, —$PO_4H_2$, —C(O)—($C_1$-$C_{10}$)alkyl, —C(O)—O($C_1$-$C_{10}$)alkyl, —C(O)—$NHR^8$, or —C(O)—$NR^8R^9$, wherein $R^8$ and $R^9$ are each independently selected from H, bond, (C1-C10)alkylene, F, Cl, Br, I, C(O), C(S), —C(S)—NH-benzyl-, —C(O)—NH-benzyl, —C(O)—($C_1$-$C_{10}$)alkylene, —$(CH_2)_p$—NH, —$(CH_2)_p$—($C_1$-$C_{10}$)alkyene, —$(CH_2)_p$—NH—C(O)—$(CH_2)_q$, —$(CH,CH_2)_r$—NH—C(O)—$(CH_2)_p$, —$(CH_2)_p$—CO—COH, —$(CH_2)_p$—CO—$CO_2H$, —$(CH_2)_p$—C(O)NH—C[$(CH_2)_q$—COH]$_3$, —C[$(CH_2)_p$ —COH]$_3$, —(CH2)$_p$-C(O)NH—C[$(CH_2)_q$—$CO_2H$]$_3$, —C[$(CH_2)_p$—$CO_2H$]$_3$ or —$(CH_2)_p$—($C_5$-$C_{14}$)heteroaryl, and b, p, q, r, t is each independently an integer selected from 0, 1, 2, 3, 4, 5, 6, 7, 8, 9, or 10.

In preferred PSMA targeting molecules, b may be an integer selected from 1, 2, 3, 4 or 5, $R^3$, $R^4$ and $R^5$ may each be $CO_2H$, X may be O.

Preferred examples of small-molecule PSMA targeting agents capable of binding to the extracellular domain of PSMA include, but are not limited to: radiolabeled N—[N—[(S)-1,3-dicarboxypropyl]carbamoyl]-S-[11C]methyl-1-cysteine (DCFBC), several urea-based peptidomimetic PSMA-inhibitors as described in Bouchelouche et al. Discov Med. 2010 January; 9(44): 55-61), including MIP-1095 (Hillier et al. Cancer Res. 2009 Sep. 1; 69(17):6932-40), and DOTA-conjugated PSMA-inhibitor PSMA-617 developed by Benešová et al (JNM 2015, 56: 914-920 and EP 2862 857 A1).

Urea-based PSMA ligands usually comprise three components: the binding motif (Glu-urea-Lys), a linker, and a radiolabel-bearing moiety (chelator molecule for radiolabeling or a prosthetic group for fluorinated agents). Examples of the most commonly used low-molecular-weight PSMA ligands are $^{123}$I-MIP-1072 and $^{123}$I-MIP-1095 (Barrett J A et al. J Nucl Med. 2013; 54:380-387; Zechmann et al., Eur J Nucl Med Mol Imaging. 2014; 41:1280-1292), chelator based PSMA-617 (Afshar-Oromieh A et al., J Nucl Med. 2015; 56:1697-1705) and PSMA-I&T (Weineisen M et al., J Nucl Med. 2015; 56:1169-1176), PSMA-I&S (Robu S et al., J Nucl Med. 2017; 58:235-242). As further $^{18}$F-labeled small-molecule urea derivatives $^{18}$F-DCFPyL (Chen Y et al., Clin Cancer Res. 2011; 17:7645-7653) and $^{18}$F-PSMA-1007 (Giesel F L et al., Eur J Nucl Med Molecular Imaging. 2017; 44:678-688) are mentioned.

Recently, Kelly et al. (Dual-Target Binding Ligands with Modulated Pharmacokinetics for Endoradiotherapy of Prostate Cancer. J Nucl Med. 2017 September; 58(9):1442-1449. doi: 10.2967/jnumed.116.188722) evaluated agents exhibiting affinity for both PSMA and for human serum albumin (HSA). The ligands developed by Kelly et al. comprise a p-(iodophenyl)butyric acid entity for HSA binding and an urea-based PSMA binding entity. In the compounds developed by Kelly et al., radiotherapeutic iodine ($^{131}$I) is covalently attached to the HSA binding moiety, which is in turn directly connected to the PSMA binding entity via a hydrocarbyl chain.

Another example is a $^{177}$Lu-labeled phosphoramidate-based PSMA inhibitor with an albumin-binding entity (Choy et al. *Theranostics* 2017; 7(7): 1928-1939). A DOTA chelator complexing the $^{177}$Lu radionuclide was ether-linked to the irreversible PSMA inhibitor CTT1298 (EP 2970345 A1).

Thus, the targeting molecule in the radiolabeled complex is preferably a PSMA-targeting molecule, which may be bound to a chelator molecule, as defined above, and complexed with a radionuclide, as defined above, e.g. $^{177}Lu$.

The targeting molecule and the chelating agent usually form together conjugates or molecules (suitable for radiolabeling). Various such conjugates/molecules are known in the art. Preferred conjugates comprising a chelating agent and a targeting molecule, which is able to bind to PSMA, are disclosed in WO 2018/215627 A1, which is incorporated herein by reference.

Preferred examples of conjugates comprising the targeting molecule and the chelating agent include PSMA-617 (shown in formula (3) below), PSMA-I&T (shown in formula (3) below) and Ibu-Dα-PSMA (shown in formula (5) below):

PSMA-617

(3)

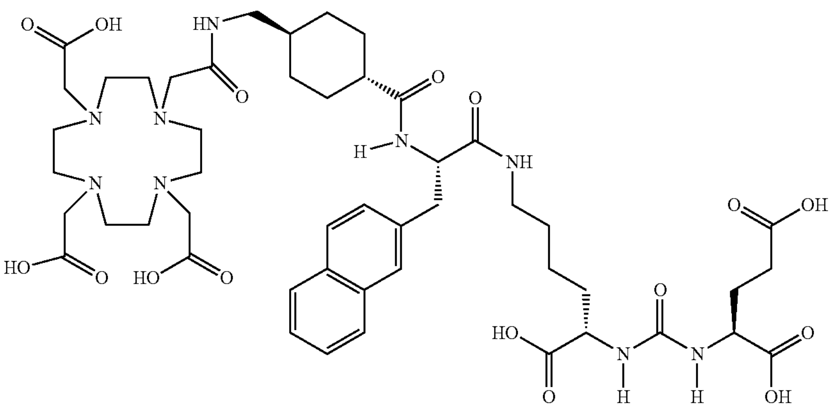

PSMA-I&T (4)

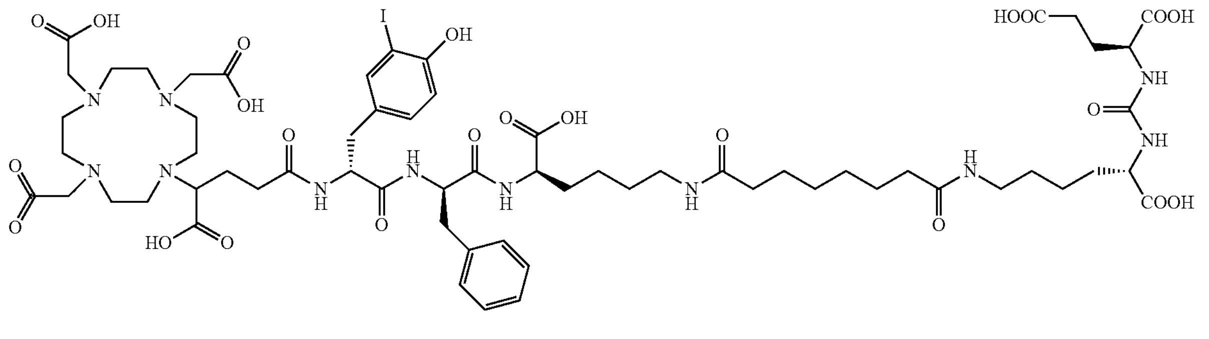

Ibu-Dα-PSMA (5)

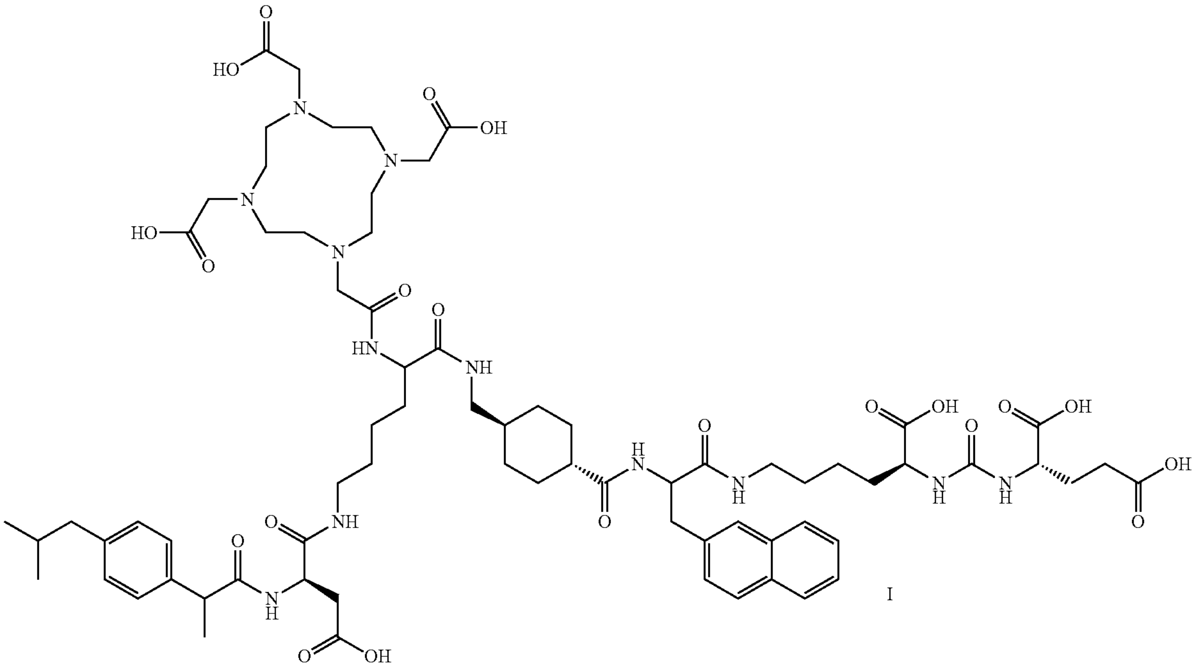

I

Somatostatin Receptor Targeting Compounds

Other particularly suitable targeting molecules bind to a somatostatin receptor. Molecules binding to a somatostatin receptor are known in the art, such as somatostatin analogues. Preferably, the targeting molecule is a somatostatin receptor binding peptide. More preferably said somatostatin receptor binding peptide is selected from octreotide, octreotate, lanreotide, vapreotide, pasireotide, ilatreotide, pentetreotide, depreotide, satoreotide, veldoreotide. Even more preferably, the targeting molecule is a somatostatin receptor binding peptide selected from octreotide and octreotate.

In particular for the treatment of well to moderately differentiated neuroendocrine tumors (NET), peptides targeting the somatostatin receptor (SSTR) maybe used. In NET, radioligand therapy is well-established and may achieve high rates of long lasting tumor remission and stabilization. Peptides targeting the somatostatin receptor are e.g. somatostatin analogs tyr3-octreotide (D-Phe-c(Cys-Tyr-D-Trp-Lys-Thr-Cys)-Thr(ol)) (SEQ ID NO:1) and tyr3-octeotrate (D-Phe-c(Cys-Tyr-D-Trp-Lys-Thr-Cys)-Thr) (SEQ ID NO:2) (Capello A et al.: Tyr3-octreotide and Tyr3-octreotate radiolabeled with $^{177}$Lu or $^{90}$Y: peptide receptor radionuclide therapy results in vitro, Cancer Biother Radiopharm, 2003 October; 18(5): 761-8). Further examples of somatostatin receptor agonists are the peptides octreotide (D-Phe-cyclo(Cys-Phe-D-Trp-Lys-Thr-Cys)Thr(ol)) (SEQ ID NO:3), and NOC (D-Phe-cyclo(Cys-1-Nal-D-Trp-Lys-Thr-Cys)Thr(ol)) (SEQ ID NO:4).

Others examples of compounds targeting the somatostatin-receptor are somatostatin antagonistic peptides such as JR10 (p-$NO_2$-Phe-c(D-Cys-Tyr-D-Aph(Cbm)-Lys-Thr-Cys)D-Tyr-$NH_2$) (SEQ ID NO:5); JR11 (Cpa-c(D-Cys-Aph(Hor)-d-Aph(Cbm)-Lys-Thr-Cys)D-Tyr-NH2) (SEQ ID NO:6); BASS (p-$NO_2$-Phe-cyclo(D-Cys-Tyr-D-Trp-Lys-Thr-Cys)D-Tyr-$NH_2$ (SEQ ID NO:7); LM3 (p-Cl-Phe-cyclo(D-Cys-Tyr-D-Aph(Cbm)-Lys-Thr-Cys)D-Tyr-$NH_2$ (SEQ ID NO:8).

Preferred examples of (radio)pharmaceuticals based on somatostatin analogues include, but are not limited to: $^{177}$Lu-DOTATOC ($^{177}$Lu-DOTA$^0$-[Tyr3]-octreotide) ($^{177}$Lu-DOTA-D-Phe-cyclo(Cys-Tyr-D-Trp-Lys-Thr-Cys]-Thr(ol) (SEQ ID NO:9), $^{177}$Lu-DOTANOC ($^{177}$Lu-DOTA-D-Phe-cyclo(Cys-1-Nal-D-Trp-Lys-Thr-Cys)Thr(ol)) (SEQ ID NO:10), $^{177}$Lu-DOTATATE ($^{177}$Lu-DOTA-D-Phe-cyclo(Cys-Tyr-D-Trp-Lys-Thr-Cys)Thr) (SEQ ID NO:11), $^{68}$Ga-DOTATOC ($^{68}$Ga-DOTA-D-Phe-cyclo(Cys-Tyr-D-Trp-Lys-Thr-Cys)Thr(ol)) (SEQ ID NO:12), $^{68}$Ga-DOTANOC ($^{68}$Ga-DOTA-D-Phe-cyclo(Cys-1-Nal-D-Trp-Lys-Thr-Cys)Thr(ol)) (SEQ ID NO:13), $^{90}$Y-DOTATOC ($^{90}$Y-DOTA-D-Phe-cyclo(Cys-Tyr-D-Trp-Lys-Thr-Cys)Thr(ol)) (SEQ ID NO:14), $^{90}$Y-DOTATATE ($^{90}$Y-DOTA-D-Phe-cyclo(Cys-Tyr-D-Trp-Lys-Thr-Cys)Thr) (SEQ ID NO:15), $^{111}$In-DTPA-octreotide ($^{111}$In-DTPA-D-Phe-cyclo(Cys-Phe-D-Trp-Lys-Thr-Cys)Thr(ol)) (SEQ ID NO:16).

Further examples of (radio)pharmaceuticals based on somatostatin analogues include, but are not limited to: $^{111}$In-DOTA-BASS ($^{111}$In-DOTA-p-$NO_2$-Phe-cyclo-(D-Cys-Tyr-D-Trp-Lys-Thr-Cys)D-Tyr-$NH_2$(SEQ ID NO:17), $^{111}$In-DOTA-JR11 ($^{111}$In-DOTA-Cpa-cyclo[D-Cys-Aph(Hor)-D-Aph(Cbm)-Lys-Thr-Cys]D-Tyr-$NH_2$) (SEQ ID NO:18), $^{68}$Ga-DOTA-JR11 (Ga-OpS201) ($^{68}$Ga-DOTA-Cpa-cyclo[D-Cys-Aph(Hor)-D-Aph(Cbm)-Lys-Thr-Cys]D-Tyr-$NH_2$) (SEQ ID NO:19), $^{68}$Ga-DODAGA-JR11 (Ga-OPS202) ($^{68}$Ga-NODAGA-Cpa-cyclo[D-Cys-Aph(Hor)-D-Aph(Cbm)-Lys-Thr-Cys]D-Tyr-$NH_2$) (SEQ ID NO:20), 177Lu-DOTA-JR11 (Lu-OPS201) (177Lu-DOTA-Cpa-cyclo[D-Cys-Aph(Hor)-D-Aph(Cbm)-Lys-Thr-Cys]D-Tyr-$NH_2$) (SEQ ID NO:21).

Thus, the targeting molecule in the radiolabeled complex is preferably a somatostatin receptor targeting molecule, which may be bound to a chelator molecule, as defined above, and complexed with a radionuclide, as defined above, e.g. $^{177}$Lu.

Preferred conjugates comprising a chelating agent and a targeting molecule, which is able to bind to a somatostatin receptor, include DOTA-OC ([DOTA$^0$,D-Phe$^1$]octreotride), DOTATOC ([DOTA$^0$,D-Phe$^1$,Tyr$^3$]octreotride; INN: edotreotide), DOTANOC ([DOTA$^0$,D-Phe$^1$,$_1$-Nal$^3$]octreotride), DOTATATE ([DOTA$^0$,D-Phe$^1$,Tyr$^3$]octreotate; INN: oxodotreotide), DOTALAN ([DOTA$^0$,D-β-Nal$^3$]octreotride), DOTAVAP ([DOTA$^0$,D-Phe$^1$,Tyr$^3$]vapreotide), satoreotide trizoxetan and satoreotide tetraxetan. More preferably, the molecule comprising a chelating agent and a targeting molecule selected from DOTATOC and DOTATATE.

Accordingly, the radiolabeled complex preferably comprises or consists of (i) the radionuclide and (ii) DOTATOC or DOTATATE. Particularly preferably, the radiolabeled complex (comprising the radionuclide, the targeting molecule and the chelating agent) is $^{177}$Lu-DOTATOC ($^{177}$Lu-edotreotide) or $^{177}$Lu-DOTATATE ($^{177}$Lu-oxodotreotide).

Folate Conjugates

Folate receptor (FR)-α attracted most interest as a tumor-associated target for targeted therapy concepts. Targeting of FR-positive tumor cells in vitro and in vivo has been exemplified by a number of research groups using folic acid conjugates with a variety of therapeutic probes. The FR has thus proven a valuable target for nuclear imagine using folic acid radioconjugates.

Preferred examples of folate conjugate radiopharmaceuticals use $^{99m}$Tc (Guo et al., J Nucl Med. 1999; 40: 1563-1569; Mathias et al., Bioconjug Chem. 2000; 11:253-257; Leamon et al., Bioconjug Chem. 2002; 13:1200-1210; Reddy et al., J Nucl. Med. 2004; 45:857-866; Müller et al., J Nucl Med Mol Imaging 2006; 33:1007-1016; Müller et al., Bioconjug Chem. 2006; 17:797-806), $^{111}$In (Siegel et al., J Nucl Med. 2003; 44:700-707), $^{66/67/68}$Ga (Mathias et al., Nucl Med Biol. 1999; 26:23-25; Mathias et al., Nucl Med Biol. 2003; 30:725-731) and $^{18}$F (Bettio et al., J Nucl Med. 2006; 47:1153-1160).

Representative folate conjugates are e.g. $^{111}$In-DTPA-folate, $^{177}$Lu-EC0800, $^{177}$Lu-cm09, $^{149/161}$Tb-cm09, $^{99m}$Tc (CO)$_3$, $^{99m}$Tc-EC20, $^{111}$In-DTPA-folate, $^{111}$In/$^{177}$Lu-DOTA-click-folate, $^{67}$Ga-DOTA-Bz-folate ($^{67}$Ga-EC0800), $^{68}$Ga-NODAGA-folate and the complex shown in below formula (6):

(6)

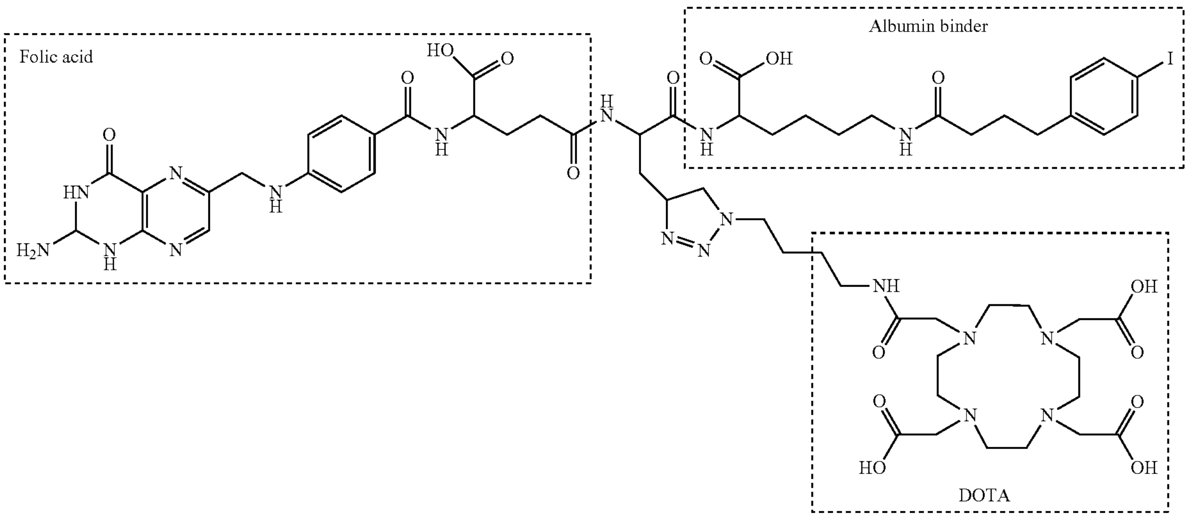

CCK2 Receptor-Targeting Compounds

The CCK2 receptor (cholecystokinin) is located in areas of the central and peripheral nervous system and is overexpressed in several types of human cancer, as medullar thyroid carcinomas, small cell lung cancers and stromal ovarian carcinomas. Research has been done on developing suitable radioligands for targeting the CCK2-receptor in vivo. A variety of radiolabeled CCK/gastrin-related peptides has been synthesized and characterized. All peptides have the C-terminal CCK receptor-binding tetrapeptide sequence Trp-Met-Asp-Phe-$NH_2$ (SEQ ID NO:27) in common or derivatives thereof. The peptides can be categorized based on the sequence of their parent peptide (gastrin or CCK) and on their form (i.e. linear, cyclic, multimers).

Examples for CCK receptor ligands are gastrin analogs, such as Sargastrin (Gln-Gly-Pro-Trp-Leu-Glu-Glu-Glu-Glu-Glu-Ala-Tyr-Gly-Trp-Nle-Asp-Phe-$NH_2$) (SEQ ID NO:22), Minigastrin 0 (MG-0) D-Glu-$(Glu)_5$-Ala-Tyr-Gly-Trp-Met-Asp-Phe-$NH_2$) (SEQ ID NO:23), Minigastrin 11 (MG-11) (D-Glu-Ala-Tyr-Gly-Trp-Met-Asp-Phe-$NH_2$) (SEQ ID NO:24), cyclo-Minigastrin 1 (cyclo-MG1) (cyclo[y-D-Glu-Ala-Tyr-D-Lys]-Trp-Met-Asp-Phe-$NH_2$) (SEQ ID NO:25), cyclo-Minigastrin 2 (cyclo-MG2) (cyclo[y-D-Glu-Ala-Tyr-D-Lys]-Trp-Nle-Asp-Phe-$NH_2$ (SEQ ID NO:26), Demogastrin 1 (D-Glu-$(Glu)_5$-Ala-Tyr-Gly-Trp-Met-Asp-Phe-$NH_2$) (SEQ ID NO:27), Demogastrin 2 (D-Glu-$(Glu)_5$-Ala-Tyr-Gly-Trp-Met-Asp-Phe-$NH_2$ (SEQ ID NO:28), H2-Met (His-His-Glu-Ala-Tyr-Gly-Trp-Met-Asp-Phe-$NH_2$) (SEQ ID NO:29), H2-Nle (His-His-Glu-Ala-Tyr-Gly-Trp-Nle-Asp-Phe-$NH_2$) (SEQ ID NO:30), H6-Met $(His)_6$-Glu-Ala-Tyr-Gly-Trp-Met-Asp-Phe-$NH_2$) (SEQ ID NO:31); and CCK8 analogs, such as CCK8 (D-Asp-Tyr-Met-Gly-Trp-Met-Asp-Phe-$NH_2$) (SEQ ID NO:32), CCK8(Nle) (D-Asp-Tyr-Nle-Gly-Trp-Nle-Asp-Phe-$NH_2$) (SEQ ID NO:33), sCCK8 (D-Asp-Tyr($OSO_3H$)-Met-Gly-Trp-Met-Asp-Phe-$NH_2$) (SEQ ID NO:24), sCCK8[$Phe^2$(p-$CH_2SO_3H$), $Nle^{3,6}$](D-Asp-Phe(p-$CH_2SO_3H$)-Nle-Gly-Trp-Nle-Asp-Phe-$NH_2$) (SEQ ID NO:35), sCCK8[$Phe^2$(p-$CH_2SO_3H$), $HPG^{3,6}$](D-Asp-Phe(p-$CH_2SO_3H$)-HPG-Gly-Trp-HPG-Asp-Phe-$NH_2$) (SEQ ID NO:36).

The CCK receptor targeting peptides are preferably radiolabeled with the radionuclides for imaging or therapeutic applications. Suitable radionuclides comprise the radionuclides specified above, and in particular comprise the radionuclides $^{99m}$Tc, $^{111}$In, $^{18}$F, $^{68}$Ga, $^{131}$I, $^{90}$Y, and $^{177}$Lu. To allow radiolabeling with a radionuclide, a chelator conjugated to the peptide is preferably used. As a chelator, the chelators specified above can be used, wherein DOTA, DOTAGA, DOTAM, DTPA and HYNIC are preferred.

Accordingly, the radiolabeled complex may include a CCK2 receptor targeting molecule, such as $^{177}$Lu-DOTA-Sargastrin, $^{111}$In-DTPA-MG0, $^{111}$In-DOTA-MG11, $^{111}$In-DOTA-MG11(Nle), $^{111}$In-DOTA-H2-Met, $^{111}$In-DOTA-H2-Nle, $^{111}$In-DOTA-H6-Met, $[^{99m}Tc]_2N_4{}^0$, D-$Glu^1$-MG ($^{99m}$Tc-Demogastrin 1), $[^{99m}Tc]_2N_4{}^{0-1}$, $Gly^0$,D-$Glu^1$-MG($^{99m}$Tc-Demogastrin 2), $^{99m}$Tc-HYNIC-MG11, $^{99m}$Tc-HYNIC-cyclo-MG1, $^{99m}$Tc-HYNIC-cyclo-MG2; and CCK8 analogs, such as $^{111}$In-DTPA-CCK8, $^{111}$In-DTPA-CCK8 (Nle), $^{99m}$Tc-HYNIC-CCK8, $^{99m}$Tc-HYNIC-sCCK8, $^{111}$In-DOTA-sCCK8[$Phe^2$(p-$CH_2SO_3H$), $Nle^{3,6}$], and $^{111}$In-DOTA-sCCK8[$Phe^2$(p-$CH_2SO_3H$), $HPG^{3,6}$].

Integrin-Binding Molecules

Integrins are heterodimeric glycoproteins consisting of an α- and β-subunit. There are 24 different combinations of the eight β-units and the eighteen α-units known. The integrins mediate cell-cell and cell-matrix interactions and transduce signals across the plasma membrane via insight-out and outside-in signaling. Some of the integrins play an important role during migration of endothelial as well as tumor cells during tumor-induced angiogenesis and tumor metastasis. Angiogenesis, the formation of new blood vessels out of the preexisting vasculature, is a critical step in the development and dissemination of various human tumors. A variety of therapeutic strategies in oncology are focused on the inhibition of tumor-induced angiogenesis. Concerning the integrins, significant attention has been paid to the role of integrin αVβ3 and αVβ5, as they are prominent on proliferating vascular endothelial cells. Thus, one of the most prominent target structures used for the development of radiopharmaceuticals for imaging angiogenesis is the integrin αVβ3.

Tumor-induced angiogenesis can be blocked in vivo by antagonizing the $\alpha_v\beta_3$ integrin with small peptides containing the Arg-Gly-Asp (RGD) amino acid sequence. This tripeptidic sequence, naturally present in extracellular matrix proteins, is the primary binding site of the $\alpha_v\beta_3$ integrin. Because of selective expression of $\alpha_v\beta_3$ integrin in tumors, radiolabeled RGD peptides are attractive candidates for $\alpha_v\beta_3$ integrin targeting in tumors. Over the last decade, many radiolabeled linear and cyclic RGD peptides have been evaluated as radiotracers for imaging tumors by SPECT or PET, as well as therapeutic agents.

Suitable radionuclides comprise the radionuclides specified above, and in particular comprise the radionuclides $^{18}$F, $^{99m}$Tc, $^{68}$Ga, $^{111}$In, $^{131}$I, $^{90}$Y, $^{67}$Cu, and $^{177}$Lu. To allow radiolabeling with a radionuclide, a chelator conjugated to the peptide is preferably used. As a chelator, any suitable the chelators, e.g. as specified above, can be used, wherein NOTA, DOTA, DOTAGA, DOTAM, DTPA, HYNIC are preferred.

Examples include $^{18}$F-Galacto-RGD, $^{99m}$Tc-NC100692 ($^{99m}$Tc-maracilatide), $^{18}$F-AH11185 ($^{18}$F-Fluciclatide), $^{18}$F-RGD-K5, $^{68}$Ga-NOTA-RGD, $^{18}$F-FPPRGD2, $^{18}$F-AlF-NOTA-PRGD2 ($^{18}$F-Alfatide), $^{18}$F-NOTA-E[PEG4-c(RGDfk)$]_2$ ($^{18}$F-Alfatide II), $^{68}$Ga-NOTA-PRGD2, $^{67}$Cu-cyclam-RAFT-c(-RGDfK-$)_4$, $^{111}$In-DOTA-E-[c(RGDfK)$]_2$, and $^{99m}$Tc-HYNIC-E-[c(RGDfK)$]_2$.

Neurotensin Receptor-Targeting Compounds

Neurotensin receptor 1 (NTR1) is overexpressed in ductal pancreatic adenocarcinoma, which is one of the deadliest cancers. Several NTR1 antagonists have been developed, such as SR142948A and SR48692, and $^{177}$Lu-3BP-2273, which is a $^{177}$Lu-labeled DOTA-conjugated NTR1 antagonist that has been developed on the basis of SR142948A. It has been used for the treatment of ductal pancreatic adenocarcinoma (Baum R P et al., The Journal of Nuclear Medicine, Vol. 59, No. 5, May 2018).

Therefore, radiopharmaceuticals may target the Neurotensin receptor 1, in particular using radiolabeled NTR1 antagonists for cancer diagnosis or therapy, preferably $^{177}$Lu- or $^{68}$Ga-labeled NTR1 antagonists, more preferably $^{177}$Lu-3BP-2273, even though other radionuclides, for example the radionuclides mentioned above, as well as other chelators, for example the chelators mentioned above, may be contemplated.

Glucagon-Like Peptide-1 (GLP-1) Receptor Targeting Compounds

The GLP-1 receptor is overexpressed on essentially all benign insulinomas and also on gastrinomas. Benign insulinomas which emerge from β-cells of the pancreas and are present as small nodules, secrete insulin leading to potentially life-threatening hypoglycemia.

Therefore, the radiopharmaceuticals may target the GLP-1 receptor. Non-limiting examples thereof include $^{111}$In-, $^{99m}$Tc-, and $^{68}$Ga-labeled peptides based on the 39-mer peptide exendin-4, such as Lys$^{40}$(Ahx-DOTA-$^{111}$In) $NH_2$-extendin-4, for example. However, other radionuclides, for example the radionuclides mentioned above, as well as other chelators, for example the chelators mentioned above, may be contemplated.

Gastrin Releasing Peptide (GRP) Receptor Targeting Compounds

GRP receptors have been demonstrated in major human tumors, such as breast cancer and prostate cancer. Bombesin is a tetradecapeptide neurohormone and an amphibian homolog of mammalian GRP (a 27mer peptide). Several bombesin analogs and bombesin antagonists have been developed and labeled with different radioisotopes (e.g. $^{68}$Ga, $^{64}$Cu, $^{18}$F) using different chelators. Examples thereof include a pan-bombesin analog $^{68}$Ga-BZH3 (Zhang H et al., Cancer Res 2004; 64: 6707-6715), and a $^{177}$Lu-labeled bombesin(7-14) derivative coupled to DOTA via a Gly-4-aminobenzoyl spacer (Bodei L et al., Eur J Nucl Med Mol Imaging 2007: 34(suppl 2): S221).

Neurokinin Type 1 Receptor Targeting Compounds

The neurokinin type 1 receptor is consistently overexpressed on glioma cells and on tumor vessels (Hennig I M et al., Int J Cancer 1995; 61: 786-792). The radiolabeled 11-amino-acid peptide substance P (Arg Pro Lys Pro Gln Gln Phe Phe Gly Leu Met) acting via the neurokinin type 1 receptor can suitably be used to target malignant gliomas. In particular, substance P has been conjugated to the chelator DOTAGA, and $^{90}$Y-labeled DOTAGA-substance P has been used in clinically studies (Kneifel S et al., Eur J Nucl Med Mol Imaging. 2007; 34: 1388-1395. In another study, the feasibility and effectiveness of targeted α-radionuclide therapy for brain tumors was assessed using the α-radiation-emitting conjugate 213Bi-DOTA-[THi8,Met(O2)11]-substance P (Cordier et al., Eur J Nucl Med Mol Imaging. 2010; 37: 1335-1344).

Therefore, the radiopharmaceuticals may target the neurokinin type 1 receptor, in particular as substance P conjugates (comprising a radionuclide, and a chelator coordinating the radionuclide).

Affilins

Affilins are artificial proteins designed to selectively bind antigens. Affilin proteins are structurally derived from human ubiquitin or gamma-B crystallin, respectively. Affilin proteins are constructed by modification of surface-exposed amino acids of these proteins and isolated by display techniques such as phage display and screening. They resemble antibodies in their affinity and specificity to antigens but not in structure, which makes them a type of antibody mimetic. Affilin® was developed by Scil Proteins GmbH as potential biopharmaceutical drugs, diagnostics and affinity ligands. Affilin molecules can be easily modified and are suitable to kill tumor cells specifically by irradiation.

Multispecific Affilin molecules can be generated, binding different targets simultaneously. Radionuclides or cytotoxins can be conjugated to Affilin proteins, making them potential tumor therapeutics and diagnostics. Radionuclide-chelator-Affilin conjugates, e.g. $^{177}$Lu-DOTA-Affilin, have been designed for therapy purposes.

Particularly suitable surface molecules are PSMA and a somatostatin receptor targeted by the targeting molecule of the radiolabeled complex. Accordingly, the targeting molecule is preferably able to bind to PSMA or a somatostatin receptor, e.g. as described above.

The targeting molecule may be either directly or indirectly (e.g., by using linkers or spacers) linked to the chelating agent. The linking bond(s) is/are covalent or non-covalent bond(s) between the targeting molecule, optionally the linker or spacer, and the chelating agent. Preferably the bond(s) is/are covalent. Preferably, the radiolabeled complex comprises linkers. Particularly suitable linkers and spacers are described in WO 2018/215627 A1, which is incorporated herein by reference, and in WO 2020/109523 A1, which is also incorporated herein by reference.

The targeting molecule and the chelating agent usually form together conjugates or molecules (suitable for radiolabeling). Various such conjugates/molecules are known in the art. Preferred conjugates comprising a chelating agent and a targeting molecule, which is able to bind to PSMA, are disclosed in WO 2018/215627 A1, which is incorporated herein by reference.

Preferred conjugates comprising a chelating agent and a targeting molecule, which is able to bind to a somatostatin receptor, include DOTA-OC ([DOTA$^0$,D-Phe$^1$]octreotride), DOTATOC ([DOTA$^0$,D-Phe$^1$,Tyr$^3$]octreotride; INN: edotreotide), DOTANOC ([DOTA$^0$,D-Phe$^1$,$_1$-Nal$^3$]octreotride), DOTATATE ([DOTA$^0$,D-Phe$^1$,Tyr$^3$]octreotate; INN: oxodotreotide), DOTALAN ([DOTA$^0$,D-β-Nal$^3$]octreotride), DOTAVAP ([DOTA$^0$,D-Phe$^1$,Tyr$^3$]vapreotide), satoreotide trizoxetan and satoreotide tetraxetan. More preferably, the molecule comprising a chelating agent and a targeting molecule selected from DOTATOC and DOTATATE.

Accordingly, the radiolabeled complex preferably comprises or consists of (i) the radionuclide and (ii) DOTATOC or DOTATATE. Particularly preferably, the radiolabeled complex (comprising the radionuclide, the targeting molecule and the chelating agent) is $^{177}$Lu-DOTATOC ($^{177}$Lu-edotreotide) or $^{177}$Lu-DOTATATE ($^{177}$Lu-oxodotreotide).

Stabilizer

In order to provide stability against radiolytic degradation, the pharmaceutical composition comprises a stabilizer. As used herein, the term "stabilizer" (against radiolytic degradation) refers to an agent which protects organic molecules against radiolytic degradation. In particular, the stabilizer may be able to scavenge radicals, which may be generated, for example, when the radionuclide emits a gamma ray and the gamma ray cleaves a bond between the atoms of organic molecules, thereby forming radicals. Therefore, the stabilizer can avoid or reduce that radicals undergo other chemical reactions, which might lead to undesired, potentially ineffective or even toxic molecules.

The stabilizer comprises ascorbic acid (L-ascorbic acid, vitamin C) and/or a salt thereof (e.g. sodium ascorbate). However, the composition is free of gentisic acid (2,5-dihydroxybenzoic acid) or a salt thereof. As shown in the appended examples, such a formulation not only decreases the complexity of the composition (and its preparation), but surprisingly even higher stability of the radiolabeled complex can be obtained.

In some embodiments, other stabilizers, except for gentisic acid or a salt thereof, may be present in addition to ascorbic acid and/or a salt thereof. Examples of such further stabilizers include methionine, histidine, melatonine, ethanol, and Se-methionine.

Preferably, the pharmaceutical composition does not comprise further stabilizers in addition to ascorbic acid and/or a salt thereof. Accordingly, ascorbic acid and/or a salt thereof are preferably the only stabilizers present in the pharmaceutical composition. In other words, the stabilizer comprised in the pharmaceutical composition preferably consists of ascorbic acid and/or a salt thereof.

Various salts of ascorbic acid are known in the art and readily available. In general, the term "salt" refers to an ionic assembly of cations and anions, which is composed of related numbers of cations and anions, so that the product (the salt) is electrically neutral (without net charge). In salts of ascorbic acid, the salts are typically formed with the ascorbate anion. Preferred salts of ascorbic acid include the alkali salts of ascorbic acid. The term "alkali salt" refers to salts that produce hydroxide ions when dissolved in water. Non-limiting examples of preferred salts of ascorbic acid include sodium, potassium, calcium, magnesium and lithium salts of ascorbic acid; such as sodium ascorbate, sodium ascorbyl phosphate, potassium ascorbate, calcium ascorbate, magnesium ascorbate, magnesium ascorbyl phosphate and lithium ascorbate. Most preferably, the salt of ascorbic acid is a sodium salt of ascorbic acid, in particular sodium ascorbate.

Composition

The pharmaceutical composition according to the present invention is preferably an aqueous solution, in particular a radiopharmaceutical aqueous solution. As used herein, an "aqueous solution" is usually a solution of one or more solute(s) in water. The pharmaceutical composition may be for intravenous (IV) use/application/administration. The pharmaceutical composition is typically stable, concentrated, and ready-to-use.

In some embodiments, the pharmaceutical composition may comprise a buffer, e.g. an acetate buffer, a citrate buffer or a phosphate buffer. However, the present inventors have surprisingly found that ascorbic acid and/or a salt thereof not only provide increased stability to the radiolabeled complex, but also function as buffer (i) during radiolabeling of the complex and (ii) in the formulation of the pharmaceutical composition (to maintain a suitable pH for parenteral injection). Therefore, additional buffers are usually not required. It is thus preferred that the composition does not contain an acetate buffer. It is also preferred that the composition does not contain a citrate buffer. It is also preferred that the composition does not contain a phosphate buffer. More preferably, the pharmaceutical composition does not contain an acetate buffer, a citrate buffer or a phosphate buffer. Even more preferably, the pharmaceutical composition does not contain any additional buffer (in addition to ascorbic acid and/or the salt thereof, which are present as stabilizer(s) and also provide buffering functionality).

In some embodiments, the pharmaceutical composition may comprise a sequestering agent, such as diethylenetriaminepentaacetic acid (DTPA) or a salt thereof. As used herein, the term "sequestering agent" refers to an agent suitable to complex the radionuclide metal ions, such as DTPA. However, the present inventors have found that addition of a sequestering agent is not required. Therefore, it is preferred, that the pharmaceutical composition does not comprise DTPA. More preferably, the pharmaceutical composition does not comprise a sequestering agent, such as DTPA. DTPA is known to induce side effects, such as nausea, vomiting, diarrhea, chills, fever, itching, muscle cramps, headache, light-headedness and chest pain.

In some embodiments, the pharmaceutical composition does not comprise physiological (saline) solution, in particular 0.9% NaCl solution (saline). In some embodiments, the pharmaceutical composition does not comprise NaCl.

It is even more preferred that the only excipients (i.e., components of the pharmaceutical composition, which are not active ingredients, such as the radiolabeled complex) comprised in the pharmaceutical composition may be ascorbic acid and/or a salt thereof; and water (e.g., (sterile) water for injection and/or highly purified water). Accordingly, the pharmaceutical composition may preferably consist (essentially) of (a) the radiolabeled complex and, optionally, one or more precursors thereof;
(b) ascorbic acid and/or a salt thereof; and
(c) water.

Preferably, the pharmaceutical composition comprises both, ascorbic acid as well as a salt thereof (as described above). Accordingly, it is particularly preferred that the pharmaceutical composition comprises ascorbic acid and sodium ascorbate (and preferably no further stabilizer as described above).

The weight ratio of the salt of ascorbic acid to ascorbic acid in the pharmaceutical composition, in particular the weight ratio (w/w) of sodium ascorbate:ascorbic acid, is preferably between 30:1 and 70:1, more preferably between 36:1 and 66:1, even more preferably between 40:1 and 60:1, still more preferably between 45:1 and 55:1, and particularly preferably between 45:1 and 50:1. Accordingly the amount (by weight) of the salt of ascorbic acid (in particular of sodium ascorbate) preferably exceeds the amount (by weight) of ascorbic acid considerably, as described above.

Accordingly, in particular if both, ascorbic acid as well as a salt thereof (in particular sodium ascorbate), are present in the pharmaceutical composition, the concentration of ascorbic acid in the composition is preferably well below the concentration of the salt of ascorbic acid (in particular sodium ascorbate).

Preferably, the concentration of ascorbic acid in the pharmaceutical composition is in the range from 0.5 to 5.0 mg/ml, preferably in the range from 0.7 to 3.0 mg/ml, more preferably in the range from 0.8 to 2.0 mg/ml, even more preferably in the range from 0.9 to 1.5 mg/ml, and still more preferably in the range from 1.0 to 1.25 mg/ml. For example, the concentration of ascorbic acid in the pharmaceutical composition may be about 1.11 mg/ml.

With regard to the concentration of the salt of ascorbic acid, it is preferred that the concentration of the salt of ascorbic acid, in particular sodium ascorbate, in the pharmaceutical composition is in the range from 10 mg/ml to 100 mg/ml, preferably in the range from 20 mg/ml to 90 mg/ml, more preferably in the range from 30 mg/ml to 80 mg/ml, even more preferably in the range from 40 mg/ml to 70 mg/ml, still more preferably in the range from 44 mg/ml to 66 mg/ml, and particularly preferably in the range from 50 mg/ml to 60 mg/ml. For example, the concentration of the salt of ascorbic acid, in particular sodium ascorbate, in the pharmaceutical composition may be about 51 mg/ml.

In some embodiments, the pharmaceutical composition is substantially free of ethanol. Higher concentrations of ethanol may be associated with tolerability issues, such that ethanol may be restricted or avoided. In some embodiments, the amount of ethanol in the pharmaceutical composition is no more than 5%, preferably no more than 2%, more preferably no more than 1% in the final pharmaceutical composition (to be injected/infused). Even more preferably, the solution is free of ethanol.

In some embodiments, the pharmaceutical composition may consist (essentially) of (a) $^{177}$Lu-DOTATOC (and one or more precursors thereof);

(b) 40 mg/ml to 70 mg/ml sodium ascorbate and 1.0 to 1.25 mg/ml ascorbic acid with a weight ratio (w/w) of sodium ascorbate:ascorbic acid in the range between 40:1 and 60:1; and (c) water.

In some embodiments, the pharmaceutical composition is substantially free of precursors of the radiolabeled complex, in particular of precursors of $^{177}$Lu-DOTATOC. In some embodiments, the amount of precursors of the radiolabeled complex, in particular precursors of $^{177}$Lu-DOTATOC in the pharmaceutical composition is no more than 5%, preferably no more than 2%, more preferably no more than 1%, even more preferably no more than 0.5% of the amount of radiolabeled complex, in particular $^{177}$Lu-DOTATOC, in the final pharmaceutical composition (to be injected/infused). Even more preferably, the pharmaceutical composition is free of precursors of the radiolabeled complex, in particular of precursors of $^{177}$Lu-DOTATOC.

As shown in the appended examples, the pharmaceutical composition according to the present invention can provide a shelf life of at least 96 h, in particular when stored at no more than 40° C. (e.g., 40° C./70% RH (relative humidity)). In some embodiments, the shelf life of the pharmaceutical composition is at least 24 h, preferably at least 48 h, more preferably at least 72 h and even more preferably at least 96 h, in particular when stored at no more than 40° C. In some embodiments, the shelf life of the pharmaceutical composition is from 24 h to 168 h, preferably from 48 h to 168 h, more preferably from 72 h to 168 h, and still more preferably from 96 h to 168 h, in particular when stored at no more than 40° C.

The use of the specific stabilizer(s) as described herein ensures high stability, at least 95%, 96%, 97%, 98%, 99% or 100% chemical stability with respect to the chemical purity for the radiolabeled complex even after 96 hours.

Moreover, the use of the specific stabilizer(s) as described herein ensures high stability, at least 95% radiochemical stability with respect to the radiochemical purity radionuclide complex. For example, for various formulations according to the present invention as described herein $^{177}$Lu-DOTATOC having at least 95% radiochemical purity was found after 96 hours, in particular when stored at no more than 40° C. More preferably, the radiochemical purity of the pharmaceutical composition can be maintained at ≥96%, even more preferably at ≥96.5%, still more preferably at ≥97% for at least 96 h, in particular when stored at 40° C. To this end, radiochemical purity may be determined by HPLC as known in the art; for example utilizing reversed phase chromatography (e.g., column: Acclaim 120, C18, 3 μm, 3×150 mm), e.g. at gradient conditions, with UV and radio-chemical detection.

The pharmaceutical composition according to the present invention may be provided as single-dose product, e.g. in a vial containing a single dose of the radiolabeled complex. To this end, the vial may contain about 10 to 25 ml of the pharmaceutical composition, preferably 15 to 20 ml of the pharmaceutical composition, more preferably 16 to 19 ml of the pharmaceutical composition, and even more preferably about 18 ml of the pharmaceutical composition. A single dose may allow delivery of 7.5 GBq±10% of radioactivity at injection time.

Preferably, each of the one or more the stabilizer(s) present in the (final) pharmaceutical composition is/are already present during complex formation (radiolabeling).

As used herein, the expression "present during complex formation" is intended to refer to such agents/compounds, which are present in the reaction mixture (also referred to as "radiolabeling composition") for the complex formation (radiolabeling). To obtain the radiolabeling reaction mixture (radiolabeling composition), the radionuclide solution is added to the solution containing the chelating agent linked to the targeting molecule (or vice versa). Accordingly, any agent/compound present during complex formation (radiolabeling), such as a stabilizer, may be contained in either the radionuclide solution, in the solution containing the chelating agent linked to the targeting molecule, or in a separate solution to be added. After obtaining the radiolabeling composition, elevated temperatures may be applied to the radiolabeling composition (including the agents/compounds comprised therein) for a defined time window to facilitate the complex formation (radiolabeling).

As described above, it is preferred that each of the one or more the stabilizer(s) present in the (final) pharmaceutical composition is/are already present during complex formation (radiolabeling). However, the concentrations and/or weight ratios of the stabilizer(s) in the radiolabeling composition (reaction mix) during complex formation (radiolabeling) are preferably distinct from the concentrations and/or weight ratios of the stabilizer(s) in the (final) pharmaceutical composition. For example, one or more of the stabilizers present during complex formation (radiolabeling) may be additionally added after the complex formation (radiolabeling).

As used herein, the expression "after the complex formation (radiolabeling)" refers to the time when the complex forming (radiolabeling) reaction is completed. For example, when elevated temperatures were applied for radiolabeling, "after the complex formation (radiolabeling)" may refer to a time when the radiolabeling composition (radiolabeling reaction mixture) is no longer exposed to an elevated temperature (for example, when ambient temperature is reached again, e.g. by cooling down the radiolabeling composition). In particular, "after the complex formation (radiolabeling)" may refer to the formulation of the (final) pharmaceutical composition, e.g. by dilution of the radiolabeling mix with water.

Accordingly, it is preferred that ascorbic acid and/or a salt thereof is/are present during complex formation (radiolabeling). It is also preferred that ascorbic acid and/or a salt thereof is/are added after complex formation (radiolabeling). More preferably, ascorbic acid and/or a salt thereof is/are present during complex formation (radiolabeling) and ascorbic acid and/or a salt thereof is/are added after complex formation (radiolabeling).

More preferably, ascorbic acid and a salt thereof, in particular sodium ascorbate, are present during complex formation (radiolabeling). Thereby, it is preferred that ascorbic acid and a salt thereof, in particular sodium ascorbate, are present during complex formation (i.e., in the radiolabeling composition) at a weight ratio (sodium ascorbate: ascorbic acid) of about 2:1 to 6:1, preferably about 3:1 to 5:1, more preferably about 3.5:1 to 4.5:1, even more preferably about 3.75:1 to 4.25:1, still more preferably about 4:1.

Preferably, ascorbic acid is present during complex formation (i.e., in the radiolabeling composition) at a concentration of 1-50 mg/ml, preferably 5-40 mg/ml, more preferably 7-30 mg/ml, even more preferably 10-20 mg/ml, still more preferably 10-15 mg/ml, such as about 13.3 mg/ml.

It is also preferred that the salt of ascorbic acid, in particular sodium ascorbate, is present during complex formation (i.e., in the radiolabeling composition) at a concentration of 10-100 mg/ml, preferably 20-80 mg/ml, more preferably 30-70 mg/ml, even more preferably 45-60 mg/ml, still more preferably 50-55 mg/ml, such as about 53.3 mg/ml.

Preferably, the salt of ascorbic acid, in particular sodium ascorbate, (but preferably not ascorbic acid) is added after complex formation (during formulation of the pharmaceutical composition).

Even more preferably, ascorbic acid and a salt thereof, in particular sodium ascorbate, are present during complex formation (radiolabeling); and the salt of ascorbic acid, in particular sodium ascorbate, (but preferably not ascorbic acid) is added after complex formation (during formulation of the pharmaceutical composition).

It is also preferred that ascorbic acid and/or a salt thereof, in particular sodium ascorbate, are the only stabilizers present during complex formation (radiolabeling) and after complex formation (e.g., during formulation of the pharmaceutical composition).

Particularly preferably, the excipients of the pharmaceutical composition consist essentially of sodium ascorbate, ascorbic acid and water (e.g., (sterile) water for injection and/or highly purified water). Accordingly, the pharmaceutical composition may preferably consist (essentially) of (a) the radiolabeled complex and, optionally, one or more precursors thereof;
(b) ascorbic acid and sodium ascorbate; and
(c) water (e.g., (sterile) water for injection and/or highly purified water).

The concentration of ascorbic acid in this pharmaceutical composition is preferably in the range from 0.9 to 1.5 mg/ml, and more preferably in the range from 1.0 to 1.25 mg/ml. For example, the concentration of ascorbic acid in the pharmaceutical composition may be 1.11 mg/ml±1.1 mg/ml. The concentration of sodium ascorbate in this pharmaceutical composition is preferably in the range from 40 mg/ml to 70 mg/ml, and more preferably in the range from 50 mg/ml to 60 mg/ml. For example, the concentration of sodium ascorbate in the pharmaceutical composition may be 51 mg/ml±5.1 mg/ml. Furthermore, it is preferred that in this pharmaceutical composition wherein the radionuclide is $^{177}$Lu, the chelating agent is DOTA and the targeting molecule is a peptide binding to PSMA or a somatostatin receptor.

The radionuclide may be present at a concentration providing volumetric radioactivity of 0.42 GBq/ml±0.04 GBq/ml.

Medical Treatment and Uses

In a further aspect, the present invention also provides the use of the pharmaceutical composition as described above in medicine. For example, the pharmaceutical composition as described above may be preferably used in the treatment or in the (in vitro) diagnosis of cancer (e.g., by using an isolated sample, for example a blood sample or tumor tissue). Accordingly, the present invention also provides a method for treating cancer or initiating, enhancing or prolonging an anti-tumor-response in a subject in need thereof comprising administering to the subject the pharmaceutical composition as described above.

It is understood that for medical purposes, the pharmaceutical composition usually comprises an effective amount of the radiolabeled complex. As used herein, "an effective amount" means an amount of the agent(s) that is sufficient to allow for diagnosis and/or significantly induce a positive modification of the disease to be treated. At the same time, however, an "effective amount" may be small enough to avoid serious side-effects, that is to say to permit a sensible relationship between advantage and risk. An "effective amount" may vary depending on the particular condition to be diagnosed or treated and also with the age and physical condition of the patient to be treated, the severity of the condition, the duration of the treatment, the nature of the accompanying therapy, of the particular pharmaceutically acceptable excipient or carrier used, and similar factors. Accordingly, an "effective amount" may be readily determined in a specific situation by the physician. In general, effective doses may be determined by routine experiments, e.g. by using animal models. Such models include, without implying any limitation, rabbit, sheep, mouse, rat, dog and non-human primate models. Therapeutic efficacy and toxicity of radiolabeled complexes can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. The data obtained from the cell culture assays and animal studies can be used in determining a dose range for use in humans. The dose of said conjugates lies preferably within a range of circulating concentrations that include the ED50 with little or no toxicity.

As used herein, the term "diagnosis" or "diagnosing" refers to act of identifying a disease from its signs and symptoms and/or as in the present case the analysis of biological markers (such as genes or proteins) indicative of the disease.

As used herein, the term "treatment" or "treating" of a disease includes preventing or protecting against the disease (that is, causing the clinical symptoms not to develop); inhibiting the disease (i.e., arresting or suppressing the development of clinical symptoms; and/or relieving the disease (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing." The term "treatment" thus includes "prophylaxis". Accordingly, the term "treatment" includes prophylactic treatment (before onset of the disease) as well as therapeutic treatment (after onset of the disease).

The pharmaceutical compositions as described herein are typically administered parenterally. Administration may preferably be accomplished systemically, for instance by intravenous (i.v.), subcutaneous, intramuscular or intradermal injection. Alternatively, administration may be accomplished locally, for instance by intra-tumoral injection. The pharmaceutical compositions as described above may be administered to a subject in need thereof several times a day, daily, every other day, weekly, or monthly.

Pharmaceutical compositions of the invention, in particular pharmaceutical compositions comprising radiolabeled complexes with a targeting molecule binding to PSMA, may be used in the treatment or diagnosis of any cancer expressing PSMA. In particular, the presence of PSMA-expressing cells or tissues may be indicative of a prostate tumor (cell), a metastasized prostate tumor (cell), a renal tumor (cell), a pancreatic tumor (cell), a bladder tumor (cell), and combinations thereof. Accordingly, the cancer is preferably prostate cancer, pancreatic cancer, renal cancer or bladder cancer.

Pharmaceutical compositions of the invention, in particular pharmaceutical compositions comprising radiolabeled complexes with a targeting molecule binding to a somatostatin receptor, may be used in the treatment or diagnosis of any cancer expressing a somatostatin receptor. Accordingly, the cancer is preferably a neuroendocrine tumor (NET). In particular, the NET may be selected from the group consisting of gastroenteropancreatic neuroendocrine tumor, carcinoid tumor, pheochromocytoma, paraganglioma, medullary thyroid cancer, pulmonary neuroendocrine tumor, thymic neuroendocrine tumor, a carcinoid tumor or a pancreatic neuroendocrine tumor, pituitary adenoma, adrenal gland tumors, Merkel cell carcinoma, breast cancer, Non-Hodgkin lymphoma, Hodgkin lymphoma, Head & Neck tumor, urothelial carcinoma (bladder), Renal Cell Carcinoma, Hepatocellular Carcinoma, GIST, neuroblastoma, bile duct tumor, cervix tumor, Ewing sarcoma, osteosarcoma, small cell lung cancer (SCLC), prostate cancer, melanoma, meningioma, glioma, medulloblastoma, hemangioblastoma, supratentorial primitive, neuroectodermal tumor, and esthesioneuroblastoma. Further non-limiting examples of NET tumors include functional carcinoid tumor, insulinoma, gastrinoma, vasoactive intestinal peptide (VIP) oma, glucagonoma, serotoninoma, histaminoma, ACTHoma, pheocromocytoma, and somatostatinoma.

The pharmaceutical composition as described above may be used for both imaging and therapeutic purposes, i.e. as a "theragnostic" agent. As used herein, the term "theragnostic" includes "therapeutic-only", "diagnostic-only" and "therapeutic and diagnostic" applications.

Accordingly, in a further aspect, the present invention also provides an (in vitro) method of detecting the presence of cancerous cells and/or tissues comprising (a) contacting said cancerous cells and/or tissues with the pharmaceutical composition of the invention and (b) applying detection means, optionally radiographic imaging, to detect said cells and/or tissues.

In the in vivo and in vitro uses and methods of the present invention, radiographic imaging may be accomplished using any means and methods known in the art. Preferably, radiographic imaging may involve positron emission tomography (PET) or single-photon emission computed tomography (SPECT). The targeted cells or tissues detected by radiographic imaging of the inventive conjugate may preferably comprise (optionally cancerous) prostate cells or tissues, (optionally cancerous) spleen cells or tissues, or (optionally cancerous) kidney cells or tissues.

Process for Preparing the Pharmaceutical Composition

In a further aspect the present invention also provides a process for preparing the pharmaceutical composition according to the present invention as described above comprising the following steps:

(i) formation of the radiolabeled complex as described above; and
(ii) formulation of the pharmaceutical composition as described above.

It is understood that the above detailed description applies accordingly to the process for preparing the pharmaceutical composition according to the present invention. For example, detailed embodiments described above for the radiolabeled complex apply accordingly to the process for preparing the pharmaceutical composition according to the present invention. Similarly, detailed embodiments described above for the formulation of the pharmaceutical composition apply accordingly to the process for preparing the pharmaceutical composition according to the present invention. As another example, also detailed embodiments described above for the radiolabeling composition (reaction mixture) apply accordingly to the process for preparing the pharmaceutical composition according to the present invention.

Accordingly, step (i), i.e. the formation of the radiolabeled complex, is preferably performed in a radiolabeling composition comprising (or consisting essentially of):

(a) the radionuclide and the targeting molecule linked to the chelating agent as described above; and
(b) a radiolabeling buffer comprising (or consisting of) water and ascorbic acid and/or a salt thereof.

In step (i) a radiolabeling reaction mixture (radiolabeling composition) is obtained by adding the radionuclide solution to the solution containing the chelating agent linked to the targeting molecule (or vice versa). In addition, the radiolabeling composition may comprise further components, such as a stabilizer, which may be contained in either the radionuclide solution, in the solution containing the chelating agent linked to the targeting molecule, or in a separate solution to be added.

Moreover, as described above, the radiolabeling composition preferably comprises a radiolabeling buffer, which may comprise (or consist of) water and ascorbic acid and/or a salt thereof, such as sodium ascorbate. Preferably, the radiolabeling composition in step (i) has a pH of about 4.0-5.5, more preferably about 4.5-5.0. The buffer is useful to maintain such an advantageous pH range.

After obtaining the radiolabeling composition, elevated temperatures may be applied to the radiolabeling composition (including the agents/compounds comprised therein) for a defined time window, in particular to facilitate the complex formation (radiolabeling). For example, a temperature in the range from 60 to 120° C., preferably from 70 to 110° C., more preferably from 80 to 100° C., in particular 87±4° C. may be applied to the radiolabeling composition in step (i). Accordingly, step (i) is particularly preferably performed at a temperature of 87±4° C. The elevated temperature may be applied for a defined time window, such as 10 to 40 min, preferably 15 to 35 min, more preferably 20 to 30 min, in particular the elevated temperature may be applied for 25±3 min.

Preferably, the radionuclide used in the process, in particular in step (i) to form the radiolabeled complex, is as described above (with the respective detailed/preferred embodiments). In particular, the radionuclide may be $^{177}$Lu. To this end, for example $^{177}LuCl_3$, such as Lutetium ($^{177}$Lu) chloride solution for radiolabeling, e.g., providing 40±4 GBq/ml in 0.04 M HCl, may be used as radionuclide solution in step (i). In the radiolabeling composition obtained in step (i), the radionuclide is preferably present at a concentration providing volumetric radioactivity of 2 to 20 GBq/mL, preferably 3 to 16 GBq/mL, more preferably 2 to 10 GBq/mL, even more preferably 4 to 12 GBq/mL, and still more preferably 6.0 to 9.5 GBq/mL. In some embodiments, the radionuclide is provided from activity reference time (ART) day 1 to day 4. In particular, the radionuclide is provided at starting activities of 6.0 to 9.5 GBq/mL, for example of 8 to 11.5 GBq per 1.1 mL to 1.2 mL (from activity reference time (ART) day 1 to day 4).

Preferably, the targeting molecule linked to the chelating agent used in the process, in particular in step (i) to form the radiolabeled complex, is as described above (with the respective detailed/preferred embodiments). In particular, the targeting molecule linked to the chelating agent may be DOTATOC. In the radiolabeling composition obtained in step (i), the targeting molecule linked to the chelating agent is preferably present at a concentration of 50 to 150 μg/ml, preferably 60 to 140 μg/ml, more preferably 70 to 130 μg/ml, even more preferably 80 to 120 μg/ml, and still more preferably the targeting molecule linked to the chelating agent is present in the radiolabeling composition at a concentration of 100±10 μg/ml.

As described above, ascorbic acid and/or a salt thereof, such as sodium ascorbate, is/are preferably present (in the radiolabeling composition) in step (i). More preferably both, ascorbic acid and a salt thereof, in particular sodium ascorbate, are preferably present (in the radiolabeling composition) in step (i). In particular, ascorbic acid and a salt thereof, in particular sodium ascorbate, may form a radiolabeling buffer. As described above, radiolabeling buffer is useful to maintain the pH of the radiolabeling composition in step (i), preferably at a range of about pH 4.0-5.5, more preferably about pH 4.5-5.0. The use of a radiolabeling buffer in step (i) has the advantage that the pH can be maintained even for different amounts of Lutetium ($^{177}$Lu) chloride solution can be used for radiolabeling, as required, while the pH is maintained. Therefore, it is not necessary to calculate a specific amount of a base depending on the specific amount of Lutetium ($^{177}$Lu) chloride solution to obtain the envisaged pH for each specific case. Even more preferably, ascorbic acid and a salt thereof, in particular sodium ascorbate, are present (in the radiolabeling composition, in particular forming the radiolabeling buffer) in step (i) at a weight ratio (sodium ascorbate:ascorbic acid) of about 2:1 to 6:1, preferably about 3:1 to 5:1, more preferably about 3.5:1 to 4.5:1, even more preferably about 3.75:1 to 4.25:1, still more preferably about 4:1.

As described above, ascorbic acid is preferably present (in the radiolabeling composition, in particular for forming the radiolabeling buffer) during step (i) at a concentration of 1-50 mg/ml, preferably 5-40 mg/ml, more preferably 7-30 mg/ml, even more preferably 10-20 mg/ml, still more preferably 10-15 mg/ml, such as about 13.3 mg/ml.

It is also preferred that the salt of ascorbic acid, in particular sodium ascorbate, is present (in the radiolabeling composition) during step (i) at a concentration of 10-100 mg/ml, preferably 20-80 mg/ml, more preferably 30-70 mg/ml, more preferably 40-65 mg/ml, even more preferably 45-60 mg/ml, still more preferably 50-60 or 50-55 mg/ml, such as about 53.3 mg/ml.

In step (ii) the (final) pharmaceutical composition is formulated, e.g. by dilution of the radiolabeling mix with water or other diluents (such as saline). Thereby, further components of the (final) pharmaceutical composition, such as one or more stabilizer(s) and/or buffer(s) may be added. In this way, a final volume (and concentration) of the pharmaceutical composition may be reached, e.g. as ready-to-use pharmaceutical composition, for example as single-dose product. To this end, a final volume of about 10 to 25 ml of the pharmaceutical composition, preferably 15 to 20 ml, more preferably 16 to 19 ml, and even more preferably about 18 ml of the pharmaceutical composition may be reached by appropriate dilution (and, optionally, addition of further components).

Step (ii) follows (directly or indirectly) after step (i), i.e. step (ii) is performed after complex formation (radiolabeling). In step (ii) the radiolabeling composition is usually no longer exposed to an elevated temperature (for example, when ambient temperature is reached again, e.g. by cooling down the radiolabeling composition).

Preferably, in step (ii) an aqueous solution of ascorbic acid and/or a salt thereof, in particular sodium ascorbate, are added to the radiolabeling composition (reaction mixture) obtained in step (i). In other words, ascorbic acid and/or a salt thereof, such as sodium ascorbate, is/are preferably added in step (ii) (to the radiolabeling composition obtained in step (i)) in order to formulate the (final) pharmaceutical composition. In particular, it is preferred that ascorbic acid and/or a salt thereof is/are present during step (i) and, additionally, added during step (ii).

More preferably, a salt of ascorbic acid as described above, in particular sodium ascorbate, (but no ascorbic acid) is added in step (ii) (to the radiolabeling composition obtained in step (i)) in order to formulate the (final) pharmaceutical composition. Accordingly, it is preferred that ascorbic acid and a salt thereof, in particular sodium ascorbate, are present during step (i), and (preferably the same) salt of ascorbic acid, in particular sodium ascorbate, (but no ascorbic acid) is added during step (ii).

In particular, in step (ii) an aqueous solution of a salt of ascorbic acid, in particular sodium ascorbate, (but no ascorbic acid) is preferably added to the radiolabeling composition (reaction mixture) obtained in step (i). Preferably, the concentration of the salt of ascorbic acid, in particular sodium ascorbate, in the solution added in step (ii) is in the range of 10-100 mg/ml, preferably 20-80 mg/ml, more preferably 30-70 mg/ml, even more preferably 40-60 mg/ml, still more preferably 45-55 mg/ml, in particular about 50 mg/ml.

It is also preferred that ascorbic acid and/or a salt thereof are the only stabilizers present during the entire process, in particular in the radiolabeling composition of step (i) as well as in the (final) pharmaceutical composition in step (ii). In other words, preferably no other stabilizers (other than ascorbic acid and/or a salt thereof, in particular sodium ascorbate) are used in the entire process, i.e. the radiolabeling composition of step (i) as well as the (final) pharmaceutical composition of step (ii) comprises no other stabilizers (other than ascorbic acid and/or a salt thereof, in particular sodium ascorbate). Even more preferably, ascorbic acid and/or sodium ascorbate are the only stabilizers present during the entire process, in particular in the radiolabeling composition of step (i) as well as in the (final) pharmaceutical composition in step (ii). In other words, preferably no other stabilizers (other than ascorbic acid and/or sodium ascorbate) are used in the entire process, i.e. the radiolabeling composition of step (i) as well as the (final) pharmaceutical composition of step (ii) comprises no other stabilizers (other than ascorbic acid and/or sodium ascorbate).

The present invention also provides a pharmaceutical composition obtained by the process of the invention as described above. Such a pharmaceutical composition typically exhibits the features of the above-described pharmaceutical composition. The present inventors have found that a pharmaceutical composition obtained as described herein has excellent stability. Furthermore, the present inventors have found that addition of a sequestering agent, such as DTPA, is not required in a pharmaceutical composition obtained as described herein.

BRIEF DESCRIPTION OF THE DRAWINGS

In the following a brief description of the appended figures will be given. The figures are intended to illustrate the present invention in more detail. However, they are not intended to limit the subject matter of the invention in any way.

EXAMPLES

Figure 1A:
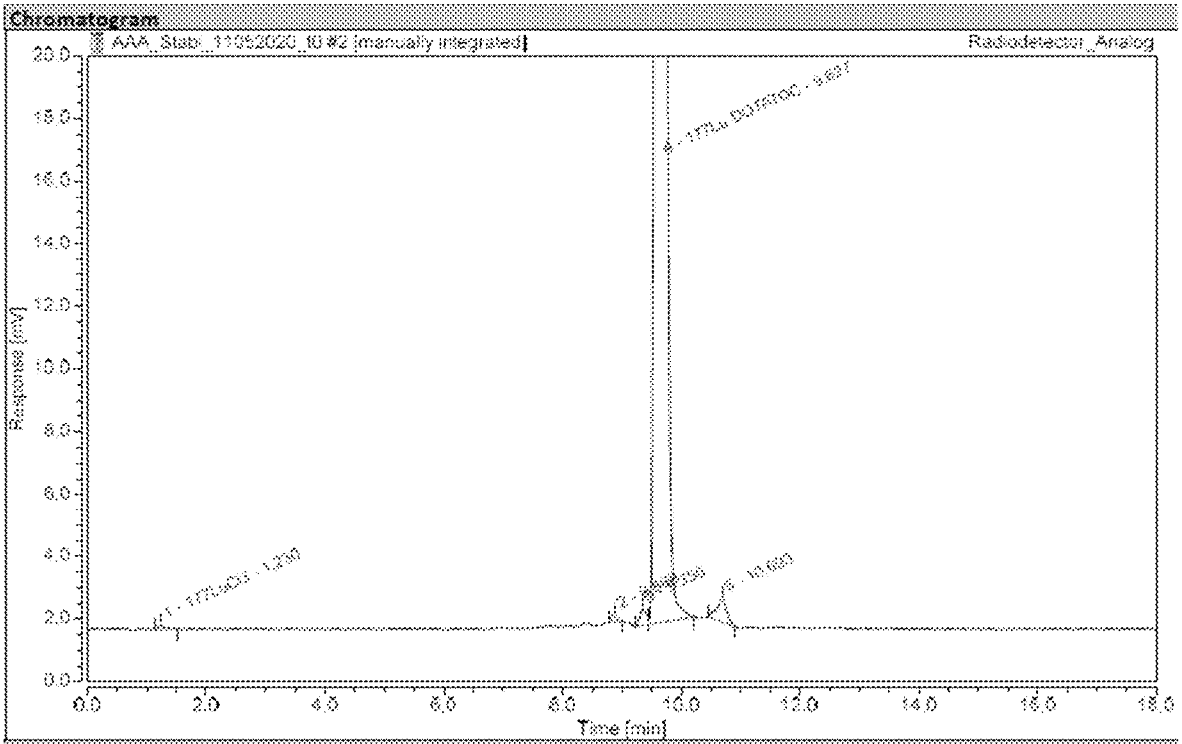
FIG. 1A shows for Example 3 the chromatogram and results obtained for a composition according to the present invention.

In the following, particular examples illustrating various embodiments and aspects of the invention are presented. However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: Effect of Various Buffer Systems on Radiolabeling Yield of [$^{177}$Lu]Lu-DOTATOC Various buffer systems of different kinds and concentrations were investigated in the radiolabeling reaction regarding the yield of radiolabeling of [$^{177}$Lu]Lu-DOTATOC. To this end, the chemical precursor DOTATOC was dissolved in different test buffers and added directly to a vial containing the radionuclide precursor $^{177}LuCl_3$ dissolved in 0.04 M HCl. The reaction mixture was heated for 15-30 min at 80-95° C. to obtain [$^{177}$Lu]Lu-DOTATOC.

Buffer systems tested and results are shown below in Table 1:

TABLE 1

| | Sodium | Ascorbic | Sodium | 0.04M | Gentisic | Acetic | | Radiochemical purity (HPLC) | |
|---|---|---|---|---|---|---|---|---|---|
| Identity (ITG F&E) | ascorbate (mg) | acid (mg) | acetate (mg) | HCl (μL) | acid (mg) | acid (μL) | pH | RP* | Free LU-177 |
| LH068 | 50 | 50 | 0 | 500 | 0 | 0 | 4.05 | 97.7% | 0.38% |
| LH055 | 80 | 20 | 0 | 500 | 0 | 0 | 4.65 | 99.2% | 0.11% |
| LH070 | 120 | 10 | 0 | 500 | 0 | 0 | 5.09 | 98.8% | 0.26% |
| LH045 | 0 | 0 | 27 | 500 | 4 | 0 | 5.18 | 96.1% | 0.15% |
| LH044 | 28.8 | 3.3 | 7.7 | 500 | 0 | 215 | 4.93 | 98.0% | 0.09% |
| LD-160429-C | 80 | 20 | 0 | 312 | 0 | 0 | 4.57 | 99.0% | 0.05% |
| LD-161216_A | 80 | 20 | 0 | 800 | 0 | 0 | 4.48 | 97.7% | 0.19% |
| LD-170601_C | 80 | 20 | 0 | 800 | 0 | 0 | 4.48 | 97.9% | 0.38% |
| LD-170601_E | 80 | 20 | 0 | 800 | 0 | 0 | 4.48 | 97.9% | 0.46% |
| LD-170601_A | 80 | 20 | 0 | 200 | 0 | 0 | 4.62 | 97.5% | 0.40% |
| LD-170601_B | 80 | 20 | 0 | 200 | 0 | 0 | 4.62 | 98.3% | 0.37% |
| LD-170601_D | 80 | 20 | 0 | 200 | 0 | 0 | 4.62 | 97.9% | 0.47% |
| No labeling | 80 | 20 | 0 | 200 | 0 | 0 | 4.62 | — | — |
| No labeling | 80 | 20 | 0 | 312 | 0 | 0 | 4.57 | — | — |
| No labeling | 80 | 20 | 0 | 800 | 0 | 0 | 4.48 | — | — |

Radiopharmaceutical ($^{177}$Lu-DOTATOC)

The results shown in Table 1 indicate that a buffer (LH045) which comprises gentisic acid, but no ascorbic acid or salt thereof, provided the least favorable results with a purity of 96.1% only. In contrast thereto, all compositions comprising ascorbic acid or a salt thereof, but no gentisic acid, resulted in purities of at least 97.5% with exemplified buffers LH055 and LD-160429-C showing the best results.

Example 2: Protective Effects of Various Formulations Regarding Auto-Radiolysis of [$^{177}$Lu]Lu-DOTATOC Next, various formulations of different kinds and concentrations were tested regarding the protective effects with regard to auto-radiolysis of [$^{177}$Lu]Lu-DOTATOC. To this end, the reaction mixture from example 1, containing [$^{177}$Lu]Lu-DOTATOC, was diluted with different formulation solutions, passed over a 0.22 μm filter into a sterile vial closed with a septum. The so formulated [$^{177}$Lu]Lu-DOTATOC was stored in overhead position at 40° C. and 70% RH (relative humidity) in a controlled climate chamber.

Formulations tested and results are shown below in Table 2 ("WFI"="sterile water for injection"):

TABLE 2

| Identity (ITG F&E) | Formulation | Peptide amount [μg/GBq] | Reaction Volume [μL] | Reaction Conditions | $t_{0h}$ (%) | $t_{24h}$ (%) | $t_{48h}$ (%) | $t_{70h}$ (%) | $t_{96h}$ (%) | Active Compound |
|---|---|---|---|---|---|---|---|---|---|---|
| CF016 | 40 mL NaCl 0.9% | 15 | 1121 | 85-90° C./ 25 min | 0.15<br>97.95 | 0.4<br>90.8 | 0.9<br>82.8 | 0.85<br>80.5 | —<br>— | Free Lu-177<br>$^{177}$Lu-DOTATOC |
| CF025-B | 39 mL NaCl 0.9%, 0.5 g Sodium Ascorbate, 15 mg Gentisic Acid * | 8 | 1000 | 98° C./ 25 min | 0.3<br>96.5 | 0.7<br>93.5 | 1<br>90.7 | —<br>— | —<br>— | Free Lu-177<br>$^{177}$Lu-DOTATOC |
| CF030-B | 36 mL NaCl 0.9%, 2.0 g Sodium Ascorbate, 2 mL EtOH (5%) * | 8 | 2000 | 90° C./ 25 min | 0.2<br>97.5 | —<br>— | —<br>— | 0.3<br>97.3 | —<br>— | Free Lu-177<br>$^{177}$Lu-DOTATOC |
| CF034-A | 9 mL NaCl 0.9%, 0.5 g Sodium Ascorbate, 5% EtOH | 8 | 1000 | 90° C./ 25 min | 0.15<br>97.15 | 0.2<br>98.1 | —<br>— | 0.35<br>97.45 | —<br>— | Free Lu-177<br>$^{177}$Lu-DOTATOC |
| LH031 | 19 mL NaCl 0.9%, 1 g Sodium Ascorbate | 15 | 1000 | 90° C./ 25 min | 0.15<br>98.3 | 0.25<br>97.75 | —<br>— | 0.4<br>97.7 | —<br>— | Free Lu-177<br>$^{177}$Lu-DOTATOC |
| LH061 | 16.5 mL WFI 1.0 g Sodium Ascorbate | 11 | 1500 | 89° C./ 25 min | 0.43<br>98.0 | —<br>— | —<br>— | —<br>— | 0.6<br>95.8 | Free Lu-177<br>$^{177}$Lu-DOTATOC |
| LH085 | 16.7 mL WFI, 0.9 g Sodium Ascorbate | 16 | 1300 | 89° C./ 25 min | 0.4<br>98.0 | 0.4<br>97.7 | —<br>— | —<br>— | 0.5<br>96.7 | Free Lu-177<br>$^{177}$Lu-DOTATOC |
| LD-161205A | 16.7 mL WFI, 0.835 g Sodium Ascorbate (50 mg/mL) | 12 | 1300 | 87° C./ 25 min | 0.15<br>98.01 | —<br>— | —<br>— | —<br>— | 0.16<br>97.3 | Free Lu-177<br>$^{177}$Lu-DOTATOC |

* 2 different vials, same reaction

The results shown in Table 2 indicate that considerable radiolysis is observed after 24-70 h if 0.9% NaCl (saline) is used without stabilizer. If the composition contains gentisic acid, such as "CF025-B", radiolysis is still considerable, in particular after 48 h. In contrast thereto, if the composition comprises ascorbic acid or a salt thereof, but no gentisic acid, a strong protective effect against radiolysis was observed, in particular at 70 or 96 h.

Example 3: Comparison of the Formulation of the Invention to a Formulation of the Prior Art Next, the protective effect of the composition of the invention was compared to a formulation of the prior art, namely, as described in U.S. Pat. No. 10,596,278 B2, which describes its formulation to maintain a radiochemical purity (RCP) of ≥95% for at least 72 h when stored at 25° C.

To this end, a $^{177}$Lu-DOTATOC composition according to the present invention was prepared as follows. For one dose, the amount of peptide (DOTATOC acetate GMP precursor) was fixed to 150 µg, 7.5±0.7 GBq at ART, which means 11.3±1.1 GBq at time of manufacturing for a 96 h shelf life. The reaction buffer contained 80±8 mg sodium ascorbate and 20±2 mg ascorbic acid. The volume of $^{177}LuCl_3$ in 0.04 N HCl ranged from 200 to 800 µL. Consequently, the labeling mixture ranged from 1.2 to 1.8 mL in a 2 mL acid washed glass vial. The labeling was performed at 87±4° C. for 25 min. Thereafter, the reaction mixture was formulated with 50 mg/mL sodium ascorbate to reach a final volume of 18 mL. The detailed amounts and activity as used are shown in Table 3 below:

TABLE 3

| | Range allowed according to Protocol | Used value |
|---|---|---|
| Labeling Reaction | | |
| Activity [177Lu]LuCl$_3$ | 10.2-12.4 GBq | 11.75 GBq |
| Volume [177Lu]LuCl$_3$ | 200-800 µL | 362 µL |
| DOTATOC Acetate GMP Precursor | 135-165 µg | 150 µg |
| Na-Ascorbate | 72-88 mg | 81 mg |
| Ascorbic Acid | 18-22 mg | 20 mg |
| Volume MQ | 900-1100 µL | 1000 µL |
| Temperature at Start of Reaction | 83-91° C. | 88.7° C. |
| Temperature at End of Reaction | 83-91° C. | 89° C. |
| Time of heating | 22-28 min | 25 min |
| Formulation | | |
| Sodium Ascorbate | 45-55 mg/mL | 50.7 mg/mL |
| WFI | 16-20 mL | 16.64 mL |

In addition, a comparative $^{177}$Lu-DOTATOC composition was prepared as described in U.S. Pat. No. 10,596,278 B2. Namely, for one dose, the amount of peptide (DOTATOC acetate GMP precursor) was fixed to 250 µg, 7.4±0.7 GBq at ART, which means 9.3±0.9 GBq at time of manufacturing for a 72 h shelf life. The reaction buffer contained 11.43 µL of acetic acid, 16.5 mg gentisic acid and 16.5 mg sodium acetate. The total reaction volume was 550 µL. The labeling was performed at 91.5° C. for 15 min. Thereafter, the reaction mixture was formulated with 70 mg ascorbic acid, 1.25 mg DTPA, 171.3 mg NaCl and 16 mg NaOH, all diluted in MQ water to reach a final volume of 25 mL. The detailed amounts and activity as used are shown in Table 4 below:

TABLE 4

| | Range allowed according to Protocol | Used value |
|---|---|---|
| Labeling Reaction | | |
| Activity [177Lu]LuCl$_3$ | 9.12-11.12 GBq | 9.311 GBq |
| Volume [177Lu]LuCl$_3$ | No data found | 124 µL |
| DOTATOC Acetate GMP Precursor | 225-275 µg | 250 µg |
| Acetic Acid | 10.8-13.2 mg | 11.4 µL (30%) |
| Gentisic Acid | 12.9-15.8 mg | 16.5 mg |
| Temperature at Start of Reaction | 90-98° C. | 91.5° C. |
| Temperature at End of Reaction | 90-98° C. | 90.2° C. |
| Time of heating | 15 min | 15 min |
| Formulation | | |
| Ascorbic Acid | 2.8 mg/mL | 70 mg/mL |
| DTPA | 0.05 mg/mL | 1.25 mg |
| NaCl | 6.85 mg/mL | 171.3 mg |
| NaOH | 0.64 mg/mL | 16 mg |
| WFI | 20.5-25 mL | 23.7 mL |

After formulation, the obtained compositions were stored at 40° C. (and at room temperature) for at least 96 h.

The obtained formulations were subjected to quality control (1) at the end of synthesis (EOS), (2) 72 h after EOS, and (3) 96 h after EOS. The quality control was performed to determine the assay, chemical purity, radiochemical purity and identity of [Lu-177]-DOTATOC in [Lu-177]-edotreotide (DOTATOC) drug products. It utilizes reversed phase chromatography (column: Acclaim 120, C18, 3 µm, 3×150 mm) at gradient conditions with UV and radiochemical detection. For quality control, the samples were diluted with 0.1 M HCl to a radioactivity concentration (RAC) of 130 MBq/mL at time of measurement. A blank run was performed prior to sample injection, to ensure that no contamination is present.

Results are shown in Table 5 below. "Sample 1" refers to the $^{177}$Lu-DOTATOC composition according to the present invention as described above, while "Sample 2" refers to the comparative $^{177}$Lu-DOTATOC composition, which was prepared as described in U.S. Pat. No. 10,596,278 B2.

TABLE 5

| Sample ID | | RRT | RCP @ EOS (Area %) | RCP @ 72 h (Area %) | RCP @ 96 h (Area %) |
|---|---|---|---|---|---|
| Sample 1 | Free 177Lu | 0.13 | 0.08 | 0.14 | 0.15 |
| | impurity | 0.92 | 0.10 | 0.26 | 0.26 |
| | impurity | 0.97 | 0.25 | 0.21 | 0.16 |
| | 177Lu-DOTATOC | 1.0 | 99.02 | 98.81 | 98.83 |
| | impurity | 1.11 | 0.55 | 0.52 | 0.6 |
| Sample 2 | Free 177Lu | 0.13 | 0.09 | 0.42 | 0.45 |
| | impurity | 0.55 | nd | nd | 0.25 |
| | impurity | 0.73 | nd | 0.12 | 0.2 |
| | impurity | 0.75 | nd | 0.17 | 0.23 |
| | impurity | 0.8 | nd | 0.13 | nd |
| | impurity | 0.83 | 0.12 | 0.36 | 0.29 |
| | impurity | 0.87 | nd | 0.40 | 0.85 |
| | impurity | 0.92 | 0.3 | 1.52 | 1.71 |
| | impurity | 0.94 | 0.17 | 0.13 | 0.23 |
| | impurity | 0.97 | 0.11 | 0.77 | 0.91 |
| | 177Lu- | 1.0 | 98.01 | 95.02 | 94.23 |

TABLE 5-continued

| Sample ID | | RRT | RCP @ EOS (Area %) | RCP @ 72 h (Area %) | RCP @ 96 h (Area %) |
|---|---|---|---|---|---|
| | DOTADOC | | | | |
| | impurity | 1.11 | 0.47 | 0.69 | 0.66 |
| | impurity | 1.15 | 0.14 | 0.15 | nd |
| | impurity | 1.72 | 0.51 | 0.12 | nd |

Figure 1B:
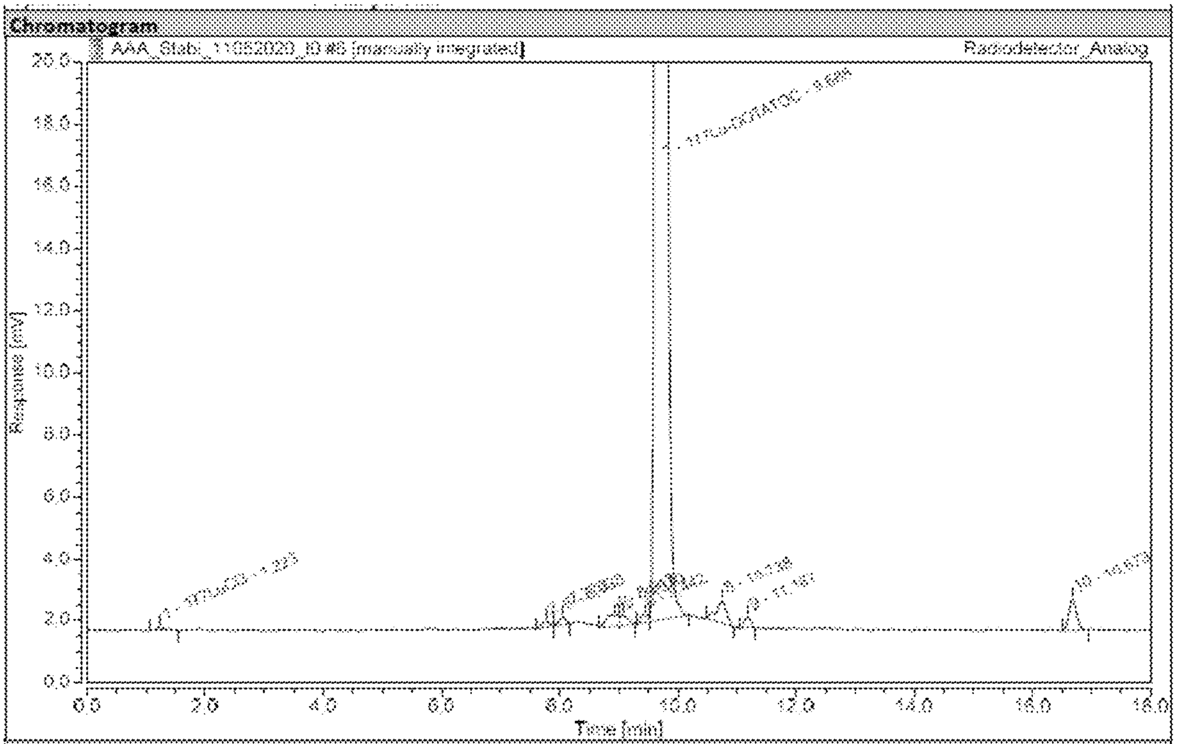
FIG. 1B shows a comparative composition according to the prior art at the end of synthesis (EOS)
Figure 2A:
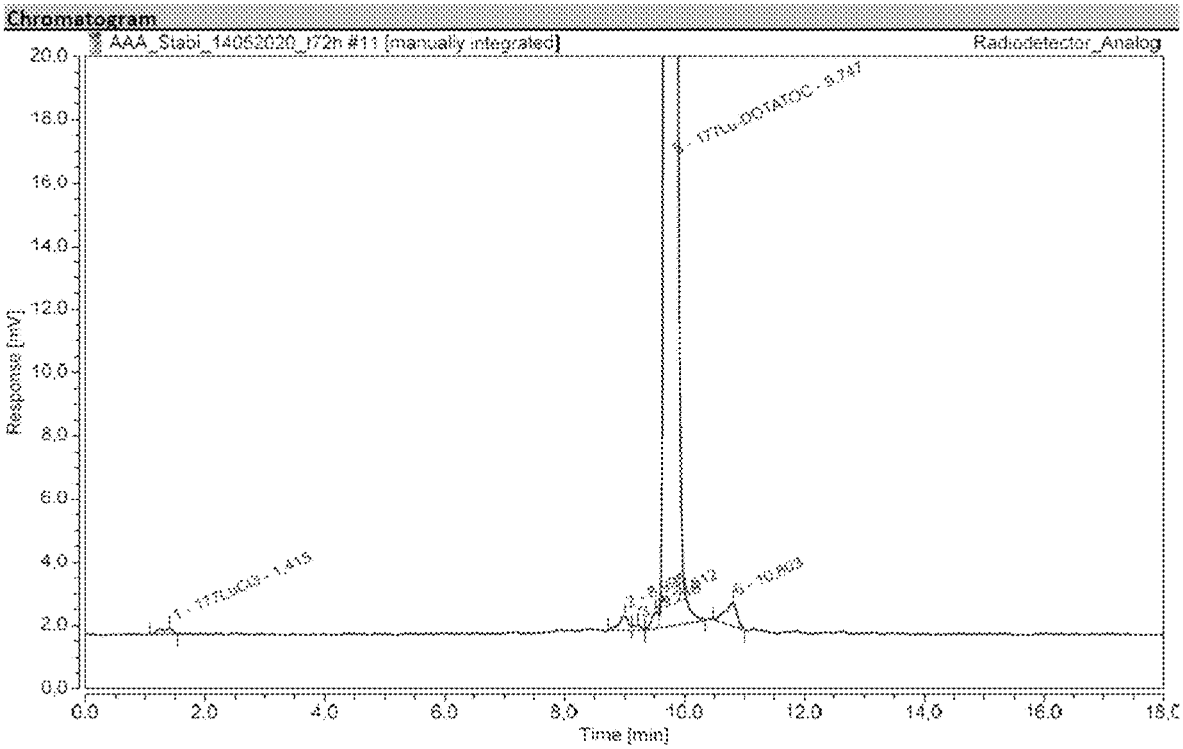
FIG. 2A shows for Example 3 the chromatogram obtained for a composition according to the present invention.
Figure 2B:
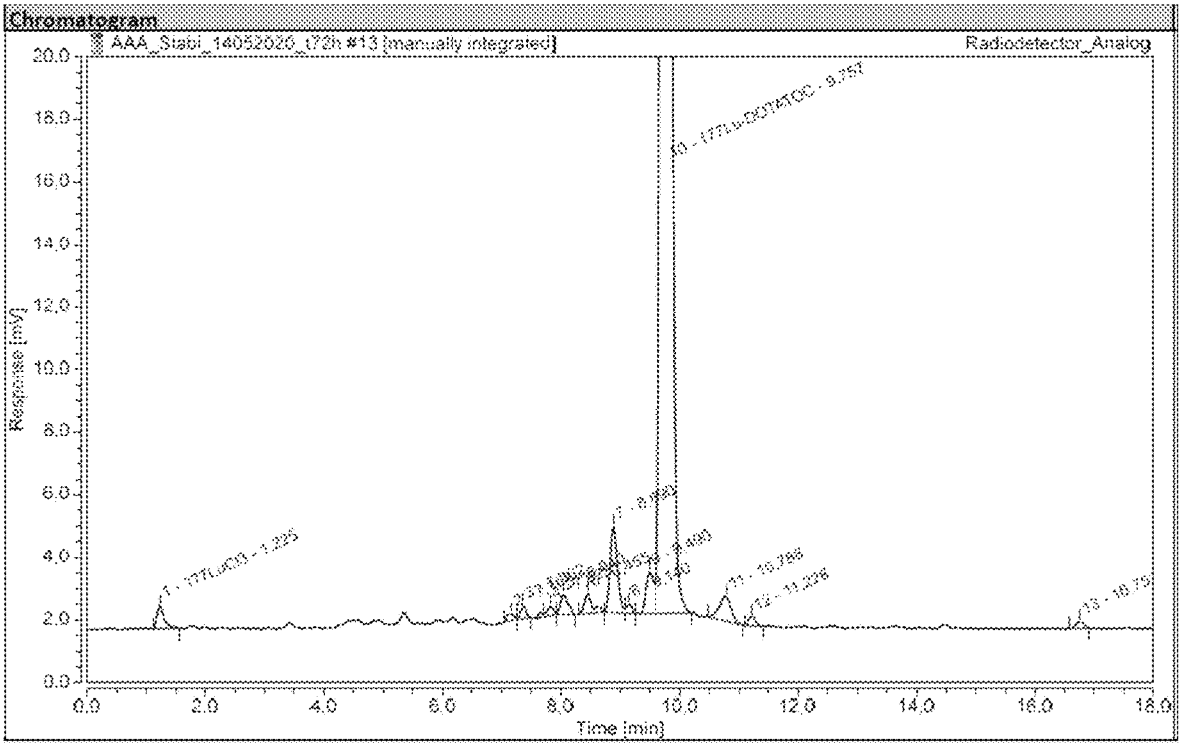
FIG. 2B shows a comparative composition according to the prior art at 72 h after the end of synthesis (EOS)
Figure 3A:
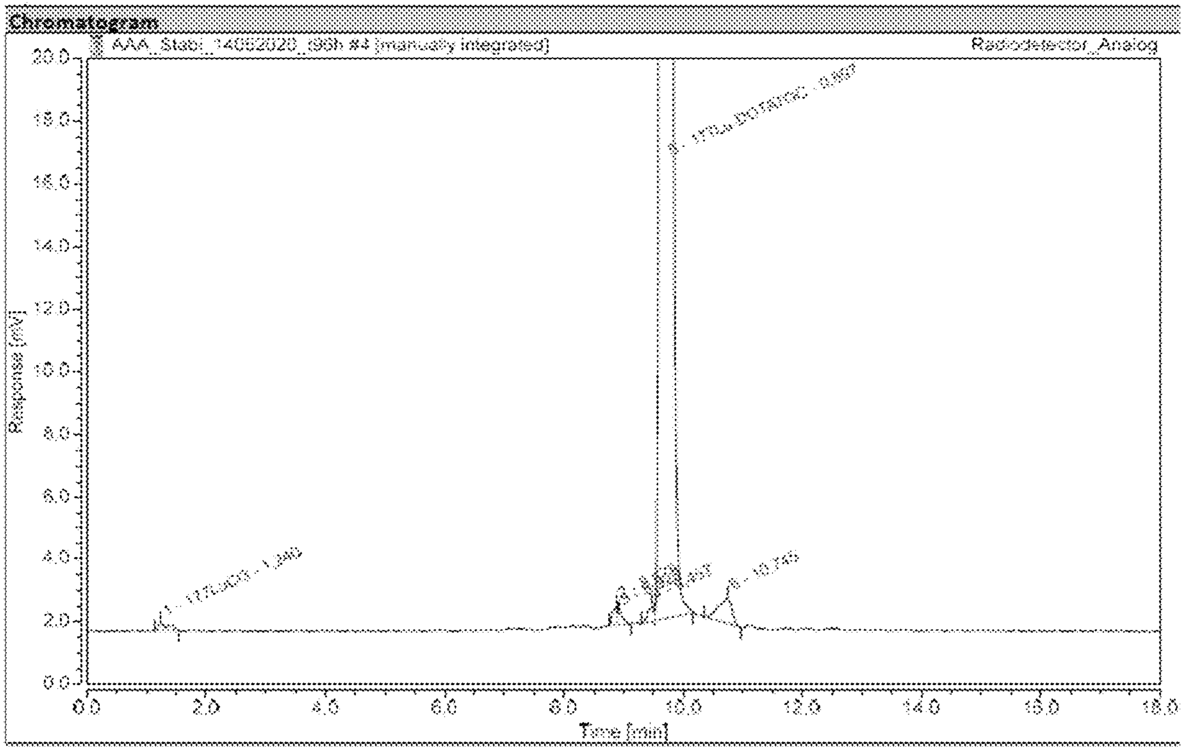
FIG. 3A shows for Example 3 the chromatogram and results obtained for a composition according to the present invention.
Figure 3B:
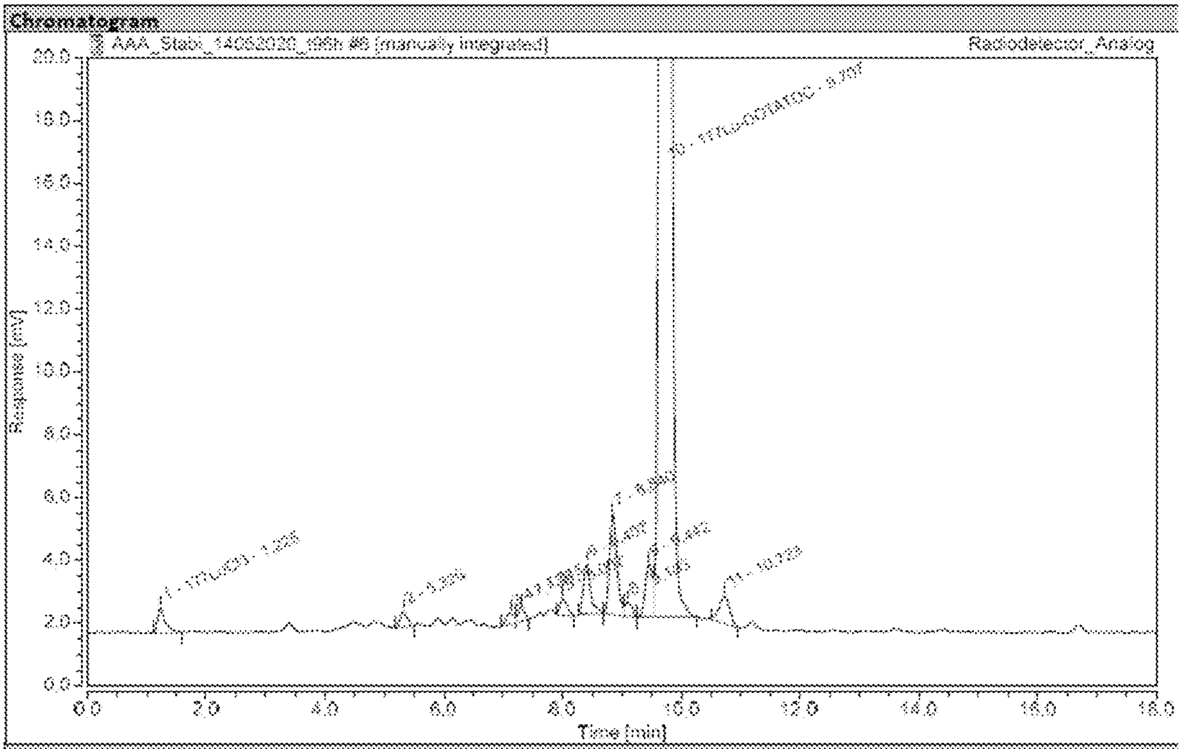
FIG. 3B shows a comparative composition according to the prior art at 96 h after the end of synthesis (EOS).

Further data as well as the chromatograms are shown in FIG. 1 (at EOS), FIG. 2 (72 h after EOS) and FIG. 3 (96 h after EOS) for the composition according to the present invention (A) and the comparative composition according to the prior art (B).

These results show the beneficial influence of the formulation according to the present invention over the prior art. In particular, the radiolysis is strongly reduced and the stability of the product is maintained, even 96 h after EOS. In the formulation according to the present invention only very few impurities are present, which are still within the specifications of ≤1.0% for each single impurity. In contrast, the formulation of the prior art (U.S. Pat. No. 10,596,278 B2) can maintain stability only until 72 h after EOS. In particular, in the comparative formulation radiolysis is clearly enhanced, which can be seen, for example, at the impurity with relative retention time (RRT) 0.92 with 1.51% at 72 h after EOS.

SEQUENCE LISTING

```
Sequence total quantity: 37
SEQ ID NO: 1            moltype = AA  length = 8
FEATURE                 Location/Qualifiers
source                  1..8
                        mol_type = protein
                        organism = synthetic construct
SITE                    1
                        note = D-phenylalanine
SITE                    4
                        note = D-tryptophan
DISULFID                2..7
                        note = intrachain
MOD_RES                 8
                        note = L-threoninol
SEQUENCE: 1
FCYWKTCT                                                                   8

SEQ ID NO: 2            moltype = AA  length = 8
FEATURE                 Location/Qualifiers
source                  1..8
                        mol_type = protein
                        organism = synthetic construct
SITE                    1
                        note = D-phenylalanine
SITE                    4
                        note = D-tryptophan
DISULFID                2..7
                        note = intrachain
SEQUENCE: 2
FCYWKTCT                                                                   8

SEQ ID NO: 3            moltype = AA  length = 8
FEATURE                 Location/Qualifiers
source                  1..8
                        mol_type = protein
                        organism = synthetic construct
DISULFID                2..7
                        note = intrachain
SITE                    1
                        note = D-phenylalanine
SITE                    4
                        note = D-tryptophan
MOD_RES                 8
                        note = L-threoninol
SEQUENCE: 3
FCFWKTCT                                                                   8

SEQ ID NO: 4            moltype = AA  length = 8
FEATURE                 Location/Qualifiers
source                  1..8
                        mol_type = protein
                        organism = synthetic construct
DISULFID                2..7
                        note = intrachain
SITE                    1
                        note = D-phenylalanine
MOD_RES                 8
                        note = L-threoninol
SITE                    3
```

-continued

```
                       note = 1-naphthyl-L-alanine
SEQUENCE: 4
FCXWKTCT                                                                8

SEQ ID NO: 5           moltype = AA  length = 8
FEATURE                Location/Qualifiers
source                 1..8
                       mol_type = protein
                       organism = synthetic construct
DISULFID               2..7
                       note = intrachain
SITE                   1
                       note = p-nitrophenylalanine
SITE                   4
                       note = 4-[Aminocarbonyl)amino-D-phenylalanine
SITE                   8
                       note = D-tyrosine amide
SITE                   2
                       note = D-cysteine
SEQUENCE: 5
XFCXKTCY                                                                8

SEQ ID NO: 6           moltype = AA  length = 8
FEATURE                Location/Qualifiers
source                 1..8
                       mol_type = protein
                       organism = synthetic construct
DISULFID               2..7
                       note = intrachain
SITE                   8
                       note = D-tyrosine amide
SITE                   4
                       note = 4-[Aminocarbonyl)amino-D-phenylalanine
SITE                   2
                       note = D-cysteine
SITE                   1
                       note = 3-cyclopropyl-L-alanine
SITE                   3
                       note =
                        [[[(4S)-hexahydro-2,6-dioxo-4-pyrimidinyl]carbonyl]amino]-L
                        -phenylalanine
SEQUENCE: 6
XCXXKTCY                                                                8

SEQ ID NO: 7           moltype = AA  length = 8
FEATURE                Location/Qualifiers
source                 1..8
                       mol_type = protein
                       organism = synthetic construct
DISULFID               2..7
                       note = intrachain
SITE                   2
                       note = D-cysteine
SITE                   1
                       note = p-nitrophenylalanine
SITE                   4
                       note = D-tryptophan
SITE                   8
                       note = L-tyrosine amide
SEQUENCE: 7
XCYWKTCY                                                                8

SEQ ID NO: 8           moltype = AA  length = 8
FEATURE                Location/Qualifiers
source                 1..8
                       mol_type = protein
                       organism = synthetic construct
DISULFID               2..7
                       note = intrachain
SITE                   1
                       note = 4-chlorophenylalanine
SITE                   2
                       note = D-cysteine
SITE                   4
                       note = 4-[Aminocarbonyl)amino-D-phenylalanine
SITE                   8
                       note = D-tyrosine amide
SEQUENCE: 8
XCYXKTCY                                                                8
```

-continued

```
SEQ ID NO: 9            moltype = AA  length = 8
FEATURE                 Location/Qualifiers
source                  1..8
                        mol_type = protein
                        organism = synthetic construct
SITE                    4
                        note = D-tryptophan
DISULFID                2..7
                        note = intrachain
SITE                    8
                        note = L-threoninol
SITE                    1
                        note = D-Phenylalanine
MOD_RES                 1
                        note = N-terminus linked via amide bond to
                         177Lu-2,2',2'',2'''-(1,4,7,10-Tetraazacyclododecane-1,4,7,1
                         0-tetrayl)tetraacetic acid
SEQUENCE: 9
FCYWKTCX                                                                8

SEQ ID NO: 10           moltype = AA  length = 8
FEATURE                 Location/Qualifiers
source                  1..8
                        mol_type = protein
                        organism = synthetic construct
DISULFID                2..7
                        note = intrachain
SITE                    1
                        note = D-Phenylalanine
SITE                    8
                        note = D-threoninol
SITE                    3
                        note = 1-naphthyl-L-alanine
MOD_RES                 1
                        note = N-terminus linked via amide bond to
                         177Lu-2,2',2'',2'''-(1,4,7,10-Tetraazacyclododecane-1,4,7,1
                         0-tetrayl)tetraacetic acid
SEQUENCE: 10
FCXWKTCX                                                                8

SEQ ID NO: 11           moltype = AA  length = 8
FEATURE                 Location/Qualifiers
source                  1..8
                        mol_type = protein
                        organism = synthetic construct
SITE                    1
                        note = D-Phenylalanine
SITE                    4
                        note = D-tryptophan
DISULFID                2..7
                        note = intrachain
MOD_RES                 1
                        note = N-terminus linked via amide bond to
                         177Lu-2,2',2'',2'''-(1,4,7,10-Tetraazacyclododecane-1,4,7,1
                         0-tetrayl)tetraacetic acid
SEQUENCE: 11
FCYWKTCT                                                                8

SEQ ID NO: 12           moltype = AA  length = 8
FEATURE                 Location/Qualifiers
source                  1..8
                        mol_type = protein
                        organism = synthetic construct
SITE                    1
                        note = D-Phenylalanine
SITE                    4
                        note = D-tryptophan
DISULFID                2..7
                        note = intrachain
SITE                    8
                        note = L-threoninol
MOD_RES                 1
                        note = N-terminus linked via amide bond to
                         68Ga-2,2',2'',2'''-(1,4,7,10-Tetraazacyclododecane-1,4,7,10
                         -tetrayl)tetraacetic acid
SEQUENCE: 12
FCYWKTCX                                                                8
```

-continued

```
SEQ ID NO: 13          moltype = AA  length = 8
FEATURE                Location/Qualifiers
source                 1..8
                       mol_type = protein
                       organism = synthetic construct
DISULFID               2..7
                       note = intrachain
SITE                   1
                       note = D-Phenylalanine
SITE                   8
                       note = D-threoninol
SITE                   3
                       note = 1-naphthyl-L-alanine
MOD_RES                1
                       note = N-terminus linked via amide bond to
                        68Ga-2,2',2'',2'''-(1,4,7,10-Tetraazacyclododecane-1,4,7,10
                        -tetrayl)tetraacetic acid
SEQUENCE: 13
FCXWKTCX                                                  8

SEQ ID NO: 14          moltype = AA  length = 8
FEATURE                Location/Qualifiers
source                 1..8
                       mol_type = protein
                       organism = synthetic construct
SITE                   1
                       note = D-Phenylalanine
SITE                   4
                       note = D-tryptophan
DISULFID               2..7
                       note = intrachain
SITE                   8
                       note = L-threoninol
MOD_RES                1
                       note = N-terminus linked via amide bond to
                        90Y-2,2',2'',2'''-(1,4,7,10-Tetraazacyclododecane-1,4,7,10-
                        tetrayl)tetraacetic acid
SEQUENCE: 14
FCYWKTCX                                                  8

SEQ ID NO: 15          moltype = AA  length = 8
FEATURE                Location/Qualifiers
source                 1..8
                       mol_type = protein
                       organism = synthetic construct
SITE                   1
                       note = D-Phenylalanine
SITE                   4
                       note = D-tryptophan
DISULFID               2..7
                       note = intrachain
MOD_RES                1
                       note = N-terminus linked via amide bond to
                        90Y-2,2',2'',2'''-(1,4,7,10-Tetraazacyclododecane-1,4,7,10-
                        tetrayl)tetraacetic acid
SEQUENCE: 15
FCYWKTCT                                                  8

SEQ ID NO: 16          moltype = AA  length = 8
FEATURE                Location/Qualifiers
source                 1..8
                       mol_type = protein
                       organism = synthetic construct
SITE                   1
                       note = D-Phenylalanine
SITE                   4
                       note = D-tryptophan
DISULFID               2..7
                       note = intrachain
SITE                   8
                       note = L-threoninol
MOD_RES                1
                       note = N-terminus linked via amide bond to
                        111In-N,N'-
b
                        is[N-(carboxymethyl)glycine]
SEQUENCE: 16
FCYWKTCX                                                  8

SEQ ID NO: 17          moltype = AA  length = 8
```

-continued

```
FEATURE                 Location/Qualifiers
source                  1..8
                        mol_type = protein
                        organism = synthetic construct
DISULFID                2..7
                        note = intrachain
SITE                    2
                        note = D-cysteine
SITE                    1
                        note = p-Nitrophenylalanine
SITE                    4
                        note = D-tryptophan
SITE                    8
                        note = L-tyrosine amide
MOD_RES                 1
                        note = N-terminus linked via amide bond to
                         111In-2,2',2'',2'''-(1,4,7,10-Tetraazacyclododecane-1,4,7,1
                         0-tetrayl)tetraacetic acid
SEQUENCE: 17
XCYWKTCX                                                            8

SEQ ID NO: 18           moltype = AA  length = 8
FEATURE                 Location/Qualifiers
source                  1..8
                        mol_type = protein
                        organism = synthetic construct
DISULFID                2..7
                        note = intrachain
SITE                    8
                        note = D-tyrosine amide
SITE                    4
                        note = 4-[Aminocarbonyl)amino-D-phenylalanine
SITE                    2
                        note = D-cysteine
SITE                    1
                        note = (S)-2-Amino-3-cyanopropionic acid
SITE                    3
                        note =
                         [[[(4S)-hexahydro-2,6-dioxo-4-pyrimidinyl]carbonyl]amino]-L
                         -phenylalanine
MOD_RES                 1
                        note = N-terminus linked via amide bond to
                         111In-2,2',2'',2'''-(1,4,7,10-Tetraazacyclododecane-1,4,7,1
                         0-tetrayl)tetraacetic acid
SEQUENCE: 18
XCXXKTCX                                                            8

SEQ ID NO: 19           moltype = AA  length = 8
FEATURE                 Location/Qualifiers
source                  1..8
                        mol_type = protein
                        organism = synthetic construct
DISULFID                2..7
                        note = intrachain
SITE                    8
                        note = D-tyrosine amide
SITE                    4
                        note = 4-[Aminocarbonyl)amino-D-phenylalanine
SITE                    2
                        note = D-cysteine
SITE                    1
                        note = (S)-2-Amino-3-cyanopropionic acid
SITE                    3
                        note =
                         [[[(4S)-hexahydro-2,6-dioxo-4-pyrimidinyl]carbonyl]amino]-L
                         -phenylalanine
MOD_RES                 1
                        note = N-terminus linked via amide bond to
                         68Ga-2,2',2'',2'''-(1,4,7,10-Tetraazacyclododecane-1,4,7,10
                         -tetrayl)tetraacetic acid
SEQUENCE: 19
XCXXKTCX                                                            8

SEQ ID NO: 20           moltype = AA  length = 8
FEATURE                 Location/Qualifiers
source                  1..8
                        mol_type = protein
                        organism = synthetic construct
DISULFID                2..7
```

-continued

```
                        note = intrachain
SITE                    8
                        note = D-tyrosine amide
SITE                    4
                        note = 4-[Aminocarbonyl)amino-D-phenylalanine
SITE                    2
                        note = D-cysteine
SITE                    1
                        note = (S)-2-Amino-3-cyanopropionic acid
SITE                    3
                        note =
                         [[[(4S)-hexahydro-2,6-dioxo-4-pyrimidinyl]carbonyl]amino]-L
                         -phenylalanine
MOD_RES                 1
                        note = N-terminus linked via amide bond to 5-carboxyl group
                         of
                         68Ga-2-(4,7-bis(carboxymethyl)-1,4,7-triazonan-1-yl)pentane
                         dioic acid
SITE                    1
                        note = N-terminus linked via amide bond to
                         68Ga-(1,4,7-triazacyclononane-1,4,7-triacetic acid
SEQUENCE: 20
XCXXKTCX                                                                    8

SEQ ID NO: 21           moltype = AA  length = 8
FEATURE                 Location/Qualifiers
source                  1..8
                        mol_type = protein
                        organism = synthetic construct
DISULFID                2..7
                        note = intrachain
SITE                    8
                        note = D-tyrosine amide
SITE                    4
                        note = 4-[Aminocarbonyl)amino-D-phenylalanine
SITE                    2
                        note = D-cysteine
SITE                    1
                        note = (S)-2-Amino-3-cyanopropionic acid
SITE                    3
                        note =
                         [[[(4S)-hexahydro-2,6-dioxo-4-pyrimidinyl]carbonyl]amino]-L
                         -phenylalanine
MOD_RES                 1
                        note = N-terminus linked via amide bond to
                         177Lu-2,2',2'',2'''-(1,4,7,10-Tetraazacyclododecane-1,4,7,1
                         0-tetrayl)tetraacetic acid
SEQUENCE: 21
XCXXKTCX                                                                    8

SEQ ID NO: 22           moltype = AA  length = 17
FEATURE                 Location/Qualifiers
source                  1..17
                        mol_type = protein
                        organism = synthetic construct
SITE                    15
                        note = L-Norleucine
SITE                    17
                        note = L-Phenylalaninamide
SEQUENCE: 22
QEPWLEEEEE AYGWXDX                                                          17

SEQ ID NO: 23           moltype = AA  length = 13
FEATURE                 Location/Qualifiers
source                  1..13
                        mol_type = protein
                        organism = synthetic construct
SITE                    1
                        note = D-glutamic acid
SITE                    13
                        note = L-Phenylalaninamide
SEQUENCE: 23
EEEEEEAYGW MDX                                                              13

SEQ ID NO: 24           moltype = AA  length = 8
FEATURE                 Location/Qualifiers
source                  1..8
                        mol_type = protein
                        organism = synthetic construct
```

-continued

```
SITE                    1
                        note = D-glutamic acid
MOD_RES                 8
                        note = Phenylalanine amide
SEQUENCE: 24
EAYGWMDF                                                            8

SEQ ID NO: 25           moltype = AA  length = 8
FEATURE                 Location/Qualifiers
source                  1..8
                        mol_type = protein
                        organism = synthetic construct
MOD_RES                 8
                        note = Phenylalanine amide
SITE                    1
                        note = D-glutamic acid
SITE                    4
                        note = D-lysine
SITE                    1..2
                        note = N-terminal amine of Ala(2) bound via amide bond to
                         gamma-carboxyl of Glu(1) side chain
SITE                    1..4
                        note = Cyclization between alpha-carboxyl of D-Glu(1) and
                         side-chain amine of D-Lys(4)
SEQUENCE: 25
EAYKWMDF                                                            8

SEQ ID NO: 26           moltype = AA  length = 8
FEATURE                 Location/Qualifiers
source                  1..8
                        mol_type = protein
                        organism = synthetic construct
MOD_RES                 8
                        note = Phenylalanine amide
SITE                    1
                        note = D-glutamic acid
SITE                    4
                        note = D-lysine
SITE                    1..2
                        note = N-terminal amine of Ala(2) bound via amide bond to
                         gamma-carboxyl of Glu(1) side chain
SITE                    1..4
                        note = Cyclization between alpha-carboxyl of D-Glu(1) and
                         side-chain amine of D-Lys(4)
SITE                    6
                        note = Nle
SEQUENCE: 26
EAYKWXDF                                                            8

SEQ ID NO: 27           moltype = AA  length = 12
FEATURE                 Location/Qualifiers
source                  1..12
                        mol_type = protein
                        organism = synthetic construct
SITE                    1
                        note = D-glutamic acid
MOD_RES                 12
                        note = L-Phenylalanine amide
SEQUENCE: 27
EEEEEEAYGM DF                                                       12

SEQ ID NO: 28           moltype = AA  length = 13
FEATURE                 Location/Qualifiers
source                  1..13
                        mol_type = protein
                        organism = synthetic construct
SITE                    1
                        note = D-glutamic acid
MOD_RES                 13
                        note = L-Phenylalanine amide
SEQUENCE: 28
EEEEEEAYGW MAF                                                      13

SEQ ID NO: 29           moltype = AA  length = 10
FEATURE                 Location/Qualifiers
source                  1..10
                        mol_type = protein
                        organism = synthetic construct
MOD_RES                 10
```

-continued

```
                        note = Phenylalanine amide
SEQUENCE: 29
HHEAYGWMDF                                                                  10

SEQ ID NO: 30           moltype = AA  length = 10
FEATURE                 Location/Qualifiers
source                  1..10
                        mol_type = protein
                        organism = synthetic construct
SITE                    1
                        note = D-glutamic acid
MOD_RES                 10
                        note = Phenylalanine amide
SITE                    8
                        note = Nle
SEQUENCE: 30
HHEAYGWXAF                                                                  10

SEQ ID NO: 31           moltype = AA  length = 14
FEATURE                 Location/Qualifiers
source                  1..14
                        mol_type = protein
                        organism = synthetic construct
MOD_RES                 14
                        note = Phenylalanine amide
SEQUENCE: 31
HHHHHHEAYG WMDF                                                             14

SEQ ID NO: 32           moltype = AA  length = 8
FEATURE                 Location/Qualifiers
source                  1..8
                        mol_type = protein
                        organism = synthetic construct
SITE                    1
                        note = D-Aspartic acid
MOD_RES                 8
                        note = L-Phenylalanine amide
SEQUENCE: 32
DYMGWMDF                                                                    8

SEQ ID NO: 33           moltype = AA  length = 8
FEATURE                 Location/Qualifiers
source                  1..8
                        mol_type = protein
                        organism = synthetic construct
SITE                    1
                        note = D-Aspartic acid
MOD_RES                 8
                        note = L-Phenylalanine amide
SITE                    3
                        note = Nle
SEQUENCE: 33
DYXGWMDF                                                                    8

SEQ ID NO: 34           moltype = AA  length = 8
FEATURE                 Location/Qualifiers
source                  1..8
                        mol_type = protein
                        organism = synthetic construct
SITE                    1
                        note = D-Aspartic acid
MOD_RES                 8
                        note = L-Phenylalanine amide
MOD_RES                 2
                        note = L-Tyrosine O-sulfate
SEQUENCE: 34
DYMGWMDF                                                                    8

SEQ ID NO: 35           moltype = AA  length = 8
FEATURE                 Location/Qualifiers
source                  1..8
                        mol_type = protein
                        organism = synthetic construct
SITE                    1
                        note = D-Aspartic acid
MOD_RES                 8
                        note = L-Phenylalanine amide
SITE                    3
                        note = Nle
```

-continued

```
SITE                6
                    note = Nle
SITE                2
                    note = para-CH2SO3H L-phenylamine
SEQUENCE: 35
DXXGWXDF                                                              8

SEQ ID NO: 36       moltype = AA  length = 8
FEATURE             Location/Qualifiers
source              1..8
                    mol_type = protein
                    organism = synthetic construct
SITE                1
                    note = D-Aspartic acid
MOD_RES             8
                    note = L-Phenylalanine amide
SITE                3
                    note = L-4-Hydroxyphenylglycine
SITE                6
                    note = L-4-Hydroxyphenylglycine
SITE                2
                    note = para-CH2SO3H L-phenylamine
SEQUENCE: 36
DXXGWXDF                                                              8

SEQ ID NO: 37       moltype = AA  length = 4
FEATURE             Location/Qualifiers
source              1..4
                    mol_type = protein
                    organism = synthetic construct
SITE                4
                    note = L-Phenylalaninamide
SEQUENCE: 37
WMDF                                                                  4
```

The invention claimed is:

1. A pharmaceutical composition comprising:

a) a radiolabeled complex comprising (i) 177Lu (Lutetium-177) and (ii) a cell-targeting molecule linked to a chelating agent; and b) a stabilizer against radiolytic degradation comprising 40 to 60 mg/ml of sodium ascorbate, and 1.11 mg/ml±1.1 mg/ml ascorbic acid, wherein the weight ratio of sodium ascorbate:ascorbic acid is between 30:1 and 70:1, wherein the composition does not comprise (i) gentisic acid or a salt thereof and does not comprise (ii) a sequestering agent, and wherein the composition retains greater than 98% radiochemical purity (RCP) for at least 96 hours after end of synthesis (EOS).

2. The pharmaceutical composition according to claim 1, wherein the chelating agent is DOTA.

3. The pharmaceutical composition according to claim 1, wherein the targeting molecule binds to PSMA or a somatostatin receptor.

4. The pharmaceutical composition according to claim 1, wherein the cell-targeting molecule linked to a chelating agent is DOTATOC or DOTATATE.

5. The pharmaceutical composition according to claim 1, wherein the composition is an aqueous solution.

6. The pharmaceutical composition according to claim 1, wherein the stabilizer consists of: 40 to 60 mg/ml of sodium ascorbate, and 1.11 mg/ml±1.1 mg/ml ascorbic acid, wherein the weight ratio of sodium ascorbate:ascorbic acid is between 30:1 and 70:1.

7. The pharmaceutical composition according to claim 1, wherein the composition comprises a buffer, the buffer comprising water and the sodium ascorbate; with the proviso that the composition does not contain another buffer.

8. The pharmaceutical composition according to claim 1, wherein the composition consists of:

a) the radiolabeled complex;
b) sodium ascorbate;
c) ascorbic acid; and
d) water.

9. The pharmaceutical composition according to claim 1, wherein the composition consists of:

a) the radiolabeled complex;
b) one or more precursors of the radiolabeled complex;
c) sodium ascorbate;
d) ascorbic acid; and
e) water.

10. The pharmaceutical composition according to claim 1, wherein the pharmaceutical composition is free of ethanol.

11. The pharmaceutical composition according to claim 1, wherein the stabilizer comprises 51 mg/ml±5.1 mg/ml of sodium ascorbate and 1.11 mg/ml±1.1 mg/ml of ascorbic acid.

12. The pharmaceutical composition according to claim 1, wherein the radionuclide is 177Lu, the chelating agent is DOTA, and the targeting molecule is a peptide binding to PSMA or a somatostatin receptor.

13. The pharmaceutical composition according to claim 12, wherein the radionuclide is present at a concentration providing volumetric radioactivity of 0.42 GBq/ml±0.04 GBq/ml.

14. A method for treatment of cancer, wherein the cancer is selected from the group consisting of: prostate cancer, pancreatic cancer, renal cancer, bladder cancer, neuroendocrine tumor, gastroenteropancreatic neuroendocrine tumor, carcinoid tumor, pheochromocytoma, paraganglioma, medullary thyroid cancer, pulmonary neuroendocrine tumor, thymic neuroendocrine tumor, a carcinoid tumor or a pancreatic neuroendocrine tumor, pituitary adenoma, adrenal gland tumors, Merkel cell carcinoma, breast cancer, non-Hodgkin lymphoma, Hodgkin lymphoma, head and neck tumor, urothelial carcinoma (bladder), renal cell carcinoma, hepatocellular carcinoma, GIST, neuroblastoma, bile duct tumor, cervix tumor, Ewing sarcoma, osteosarcoma, small cell lung cancer (SCLC), prostate cancer, melanoma, meningioma, glioma, medulloblastoma, hemangioblastoma, supratentorial primitive, neuroectodermal tumor, esthesioneuroblastoma, functional carcinoid tumor, insulinoma, gastrinoma, vasoactive intestinal peptide (VIP) oma, glucagonoma, serotoninoma, histaminoma, ACTHoma, pheocromocytoma, and somatostatinoma, the method comprising administering a dose of a pharmaceutical composition according to claim 1 to a subject in need thereof.

15. The method for treatment of cancer according to claim 14, wherein the dose provides delivery of 7.5 GBq±10% of radioactivity at injection time, and/or wherein the pharmaceutical composition is provided in a volume of 15 to 20 ml.

16. A process for preparing the pharmaceutical composition according to claim 1 comprising the following steps:

i) formation of the radiolabeled complex comprising (i) 177Lu (Lutetium-177) and (ii) a cell-targeting molecule linked to a chelating agent; and ii) formulation of the pharmaceutical composition by addition of sodium ascorbate and ascorbic acid to a concentration of 40 to 60 mg/ml of sodium ascorbate, and to a concentration of 1.11 mg/ml±1.1 mg/ml ascorbic acid, wherein the weight ratio of sodium ascorbate: ascorbic acid is between 30:1 and 70:1, wherein step (i) is performed in a radiolabeling composition comprising:

a) the 177Lu and the cell-targeting molecule linked to the chelating agent; and b) a radiolabeling buffer comprising water, sodium ascorbate and ascorbic acid, wherein the pharmaceutical composition does not comprise (i) gentisic acid or a salt thereof and does not comprise (ii) a sequestering agent, and wherein the composition retains greater than 98% radiochemical purity (RCP) for at least 96 hours after end of synthesis (EOS).

17. The process according to claim 16, wherein the radionuclide is present in the radiolabeling composition at a concentration providing volumetric radioactivity of 6.0 to 9.5 GBq/mL.

18. The process according to claim 16, wherein the chelating agent is DOTA, and/or wherein the targeting molecule binds to PSMA or a somatostatin receptor, wherein the targeting molecule linked to the chelating agent is present in the radiolabeling composition at a concentration of 100±10 μg/ml.

19. The process according to claim 16, wherein the sodium ascorbate, and ascorbic acid are present during step (i) at a weight ratio (sodium ascorbate:ascorbic acid) of 2:1 to 6:1, and ascorbic acid is present during step (i) at a concentration of 1-50 mg/ml, and wherein the sodium ascorbate is present during step (i) at a concentration of 10-100 mg/ml.

20. The process according to claim 16, wherein the radiolabeling composition in step (i) has a pH of 4.0-5.5, and/or wherein step (i) is performed at a temperature of 87±4° C., and/or wherein step (i) is performed for 25±3 min.

* * * * *